(12) United States Patent
Kober et al.

(10) Patent No.: US 11,995,237 B1
(45) Date of Patent: May 28, 2024

(54) ARM-WEARABLE DEVICE FOR SENSING NEUROMUSCULAR SIGNALS USING A SHARED REFERENCE ELECTRODE THAT IS SHARED BETWEEN TWO OR MORE ELECTRODES AND METHODS OF USE THEREOF

(71) Applicant: Meta Platforms Technologies, LLC, Menlo Park, CA (US)

(72) Inventors: Steven Joseph Kober, New Canaan, CT (US); Jess Brandon Pool, Garnet Valley, PA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 17/887,342

(22) Filed: Aug. 12, 2022

Related U.S. Application Data

(60) Provisional application No. 63/233,170, filed on Aug. 13, 2021.

(51) Int. Cl.
*G06F 3/01* (2006.01)
*A61B 5/00* (2006.01)
(Continued)

(52) U.S. Cl.
CPC .............. *G06F 3/015* (2013.01); *A61B 5/296* (2021.01); *A61B 5/313* (2021.01); *A61B 5/395* (2021.01);
(Continued)

(58) Field of Classification Search
CPC .......... G06F 3/015; G06F 3/014; G06F 1/163; A61B 5/395; A61B 5/296; A61B 5/313; A61B 5/7203
See application file for complete search history.

(56) References Cited

U.S. PATENT DOCUMENTS

2012/0257339 A1 10/2012 Leyde et al.
2018/0153430 A1* 6/2018 Ang ..................... A61B 5/24
(Continued)

FOREIGN PATENT DOCUMENTS

EP 2818103 A1 12/2014
WO 2019043147 A1 3/2019

OTHER PUBLICATIONS

International Search Report and Written Opinion for International Application No. PCT/US2023/013414, dated Jun. 22, 2023, 13 pages.

*Primary Examiner* — Robert J Michaud
(74) *Attorney, Agent, or Firm* — Morgan, Lewis & Bockius LLP

(57) ABSTRACT

An arm-wearable device for sensing neuromuscular signals using a shared reference electrode that is shared between two or more electrodes is provided. The arm-wearable device includes a structure configured to be worn by a user, the structure having an interior surface configured to contact a user's skin when the arm-wearable device is donned by the user. The arm-wearable device includes a first electrode, a second electrode, and a shared reference electrode, each electrode contacts the user's skin above respective neuromuscular pathways of the user when the wearable structure is worn by the user. The first and second electrodes detect neuromuscular signals and the shared reference electrode detects a reference neuromuscular signal. The arm-wearable device includes circuitry configured to compare the neuromuscular signals and the reference neuromuscular signal to determine a motor action that the user intends to perform with their hand.

20 Claims, 22 Drawing Sheets

(51) Int. Cl.
  *A61B 5/296* (2021.01)
  *A61B 5/313* (2021.01)
  *A61B 5/395* (2021.01)
  *G06F 1/16* (2006.01)

(52) U.S. Cl.
  CPC ............ *A61B 5/7203* (2013.01); *G06F 1/163* (2013.01); *G06F 3/014* (2013.01)

(56) References Cited

U.S. PATENT DOCUMENTS

2020/0138313 A1* 5/2020 Clements ............. A61B 5/6824
2021/0259638 A1 8/2021 Do Valle et al.

* cited by examiner

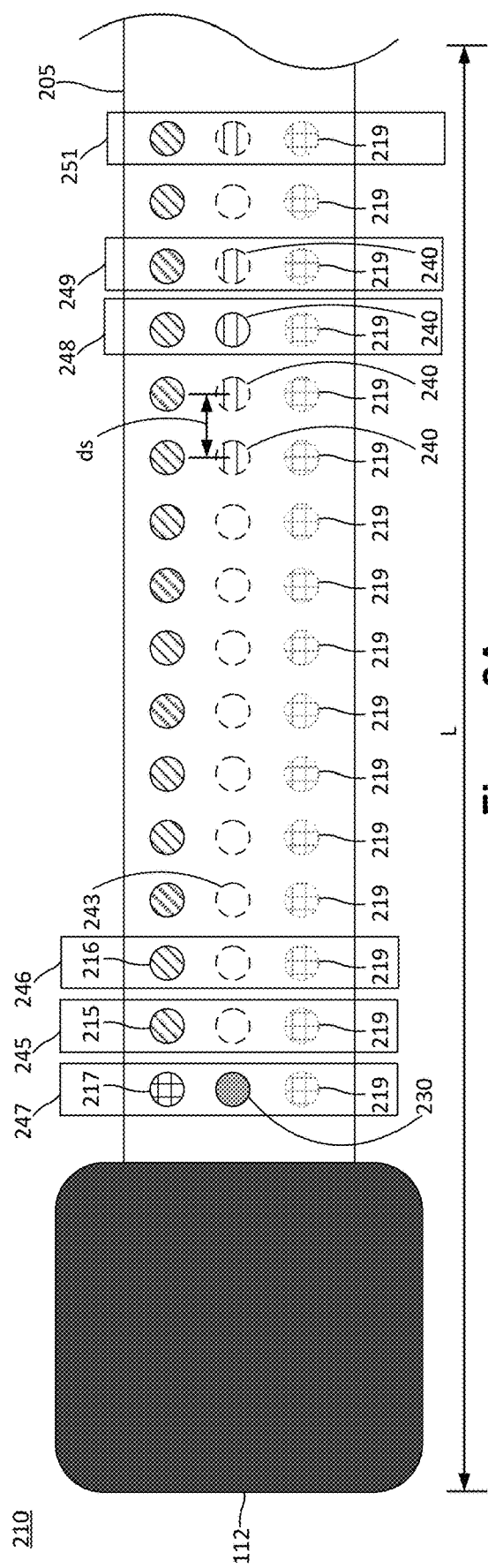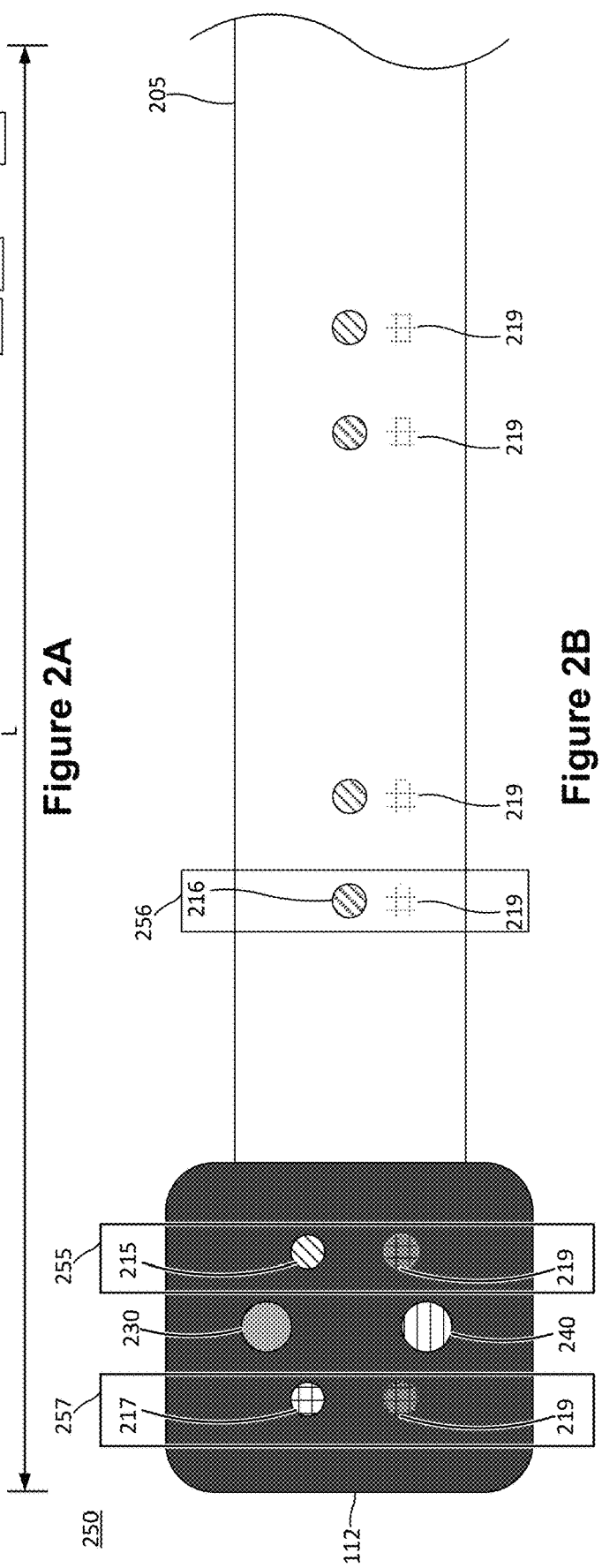

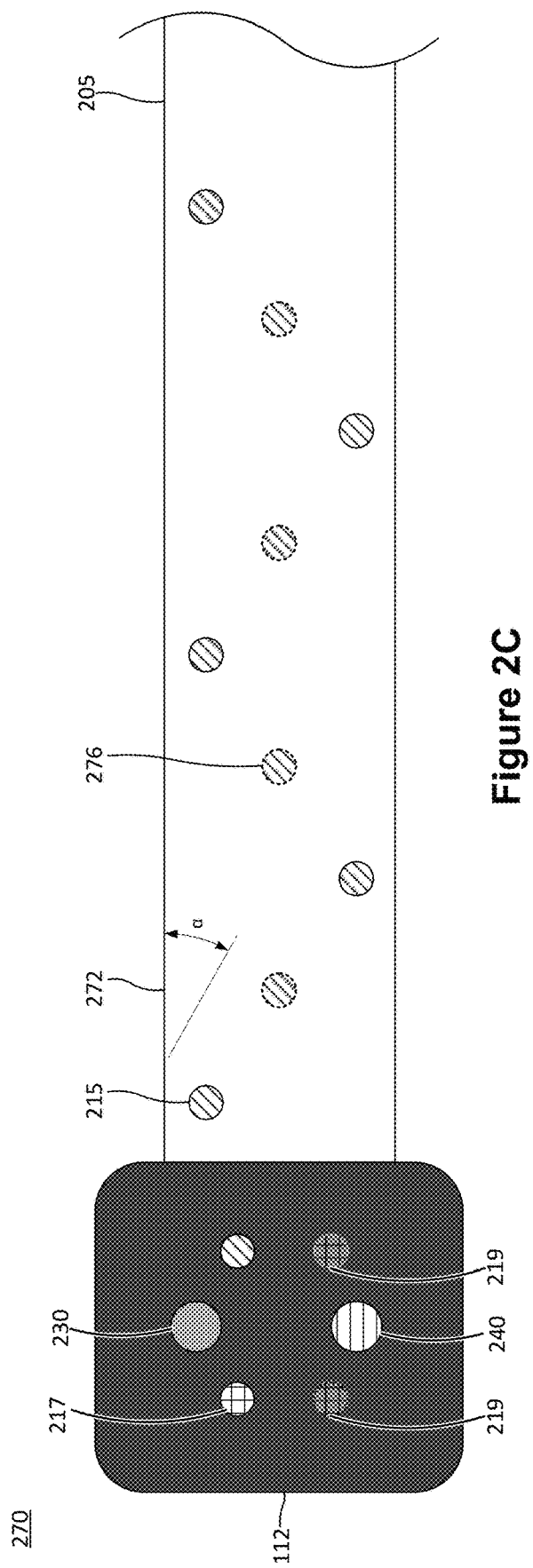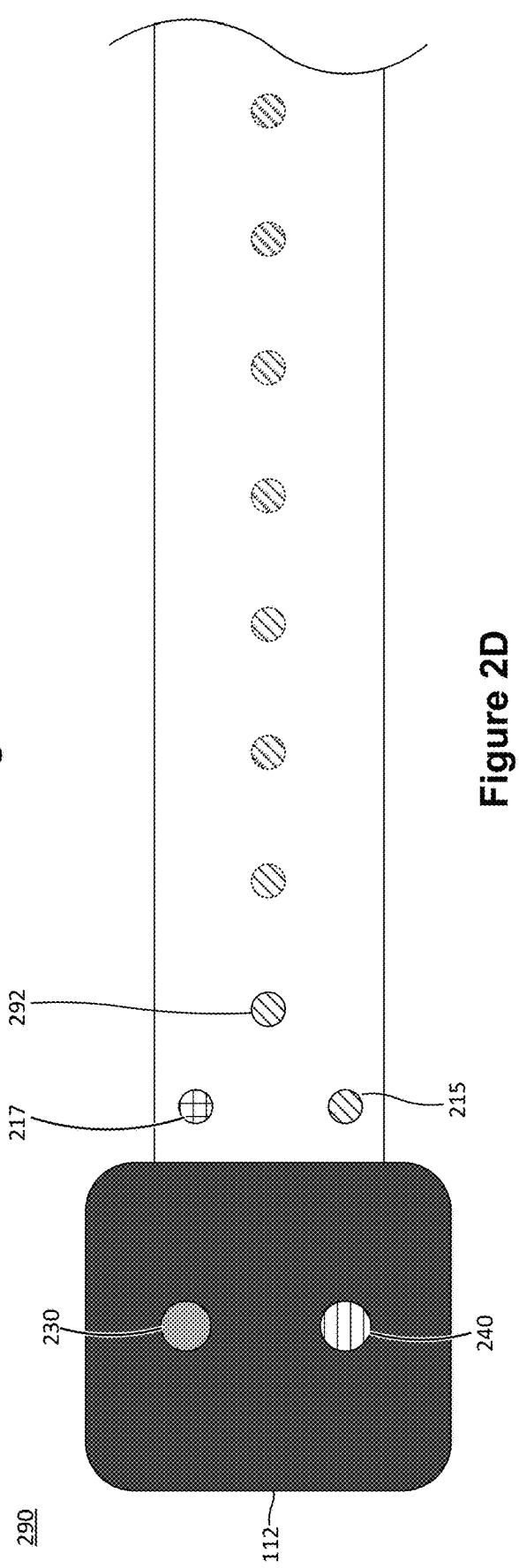

1000

1002
Contact a user's skin with the interior surface when the arm-wearable device is donned by the user, the arm-wearable device including a first electrode, a second electrode, and a shared reference electrode

1004
A portion of each electrode of the first electrode, the second electrode, and the shared reference electrode contacts the user's skin above respective neuromuscular pathways of the user when the wearable structure is worn by the user

1005
The neuromuscular pathways are associated with muscles used for moving at least each of the user's digits, the user's wrist, and the user's forearm

1006
Detect, via the first electrode and second electrode, neuromuscular signals from the respective neuromuscular pathways of the user

1008
Detect, via the shared reference electrode, a reference neuromuscular signal from neuromuscular pathways of the user that is compared to respective neuromuscular signals detected by the first electrode and the second electrode

1010
Compare, by circuity in the arm-wearable device, (i) the respective neuromuscular signals detected by the first electrode to the reference neuromuscular signal and (ii) the respective neuromuscular signals detected by the second electrode to the reference neuromuscular signal to allow for a determination by one or more processors of the arm-wearable device of a motor action that the user intends to perform with their hand

1014
The motor action is associated with one or more input commands, and providing, by the one or more processors, the one or more input commands associated with the motor action to a computing device to cause the computing device to perform the one or more input commands in an artificial-reality environment

1016
The motor action is associated with one or more user interface control commands, and causing, by the one or more processors, the performance of the one or more user interface control commands in the user interface presented at a display of a capsule of an arm-wearable device based on the motor action

```
1102
Provide a wearable structure configured to be worn by a user, the wearable
structure having an interior surface and an exterior surface, the interior surface
being configured to contact a user's skin when the arm-wearable device is donned
by the user
```

```
1104
Provide a first electrodes, a second electrode, and a shared reference electrode 1106
  The first electrode is at a first portion of the interior surface to form a first
  channel for detecting neuromuscular signals 1108
  The second electrode is at a second portion, distinct from the first portion, of
  the interior surface to form a second channel for detecting neuromuscular
  signals 1110
  The shared reference electrode is at a portion, distinct from the first and
  second portions, of the interior surface for detecting a reference
  neuromuscular signal that is compared to respective neuromuscular signals
  detected by the first electrode and the second electrode 1112
    The reference neuromuscular signal is unbuffered 1114
    The reference neuromuscular signal is buffered 1115
  Each electrode of the first electrode, the second electrode, and the shared
  reference electrode contacts the user's skin above respective neuromuscular
  pathways of the user when the wearable structure is worn by the user
```

1202
Contact a user's skin with the interior surface when the arm-wearable device is donned by the user, the interior surface including a predetermined number of channels, each channel formed by an electrode at a respective portion of the interior surface

1204
Each electrode contacts the user's skin above respective neuromuscular pathways of the user when the wearable structure is worn by the user

1205
The neuromuscular pathways are associated with muscles used for moving at least each of the user's digits, the user's wrist, and the user's forearm

1206
Detect, via the electrodes forming the predetermined number of channels, neuromuscular signals from the respective neuromuscular pathways of the user

1208
Determine a first plurality of signal differentials between respective neuromuscular signal values sensed by electrodes of each respective channel of the predetermined number of channels

1210
Each signal differential of the first plurality of signal differentials providing intra-channel information concerning neuromuscular activity in a widthwise direction of the interior surface of the wearable structure

1214
Determine, for each channel of the predetermined number of channels, a signal average based on the respective neuromuscular signal values sensed by electrodes of a respective channel of the predetermined number of channels

1216
Each respective signal average based on respective neuromuscular signal values sensed by electrodes of a respective channel of the predetermined number of channels is an average voltage measured with respect to ground

1302
Provide a wearable structure configured to be worn by a user, the wearable structure having an interior surface and an exterior surface, the interior surface being configured to contact a user's skin when the arm-wearable device is donned by the user

1304
Provide a predetermined number of channels each formed by electrodes at a respective portions of the interior surface and configured to detect neuromuscular signals

1306
Each electrode contacts the user's skin above respective neuromuscular pathways of the user when the wearable structure is worn by the user (A)

Figure 13A

ARM-WEARABLE DEVICE FOR SENSING NEUROMUSCULAR SIGNALS USING A SHARED REFERENCE ELECTRODE THAT IS SHARED BETWEEN TWO OR MORE ELECTRODES AND METHODS OF USE THEREOF

CROSS-REFERENCE TO RELATED APPLICATIONS

This application claims priority to U.S. Prov. App. No. 63/233,170, filed on Aug. 13, 2021, and entitled "Arm-Wearable Device For Sensing Neuromuscular Signals Using A Shared Reference Electrode, Sensing Neuromuscular Signals Along Both Widthwise And Radial Directions Of A Wearable Structure, And Methods Of Use Thereof," which is incorporated herein by reference.

TECHNICAL FIELD

The present disclosure relates generally to wearable devices and methods for sensing neuromuscular signals (e.g., which can be analyzed to determine motor actions that the user intends to perform with their hand) and, more particularly, to arm-wearable devices for sensing neuromuscular signals using a shared reference electrode, as well as sensing neuromuscular signals along both widthwise and radial directions of a wearable structure (e.g., a band associated with the wrist-wearable device that can use various electrodes for neuromuscular-signal-sensing purposes, as is explained below).

BACKGROUND

Some wearable devices include sensors for sensing neuromuscular signals (e.g., surface electromyography signals) to allow the devices to predict motor actions a user intends to perform. These sensors can have different performance characteristics based on a variety of factors, including user-specific factors (which can be demographically-based), such as age, body fat, hair density, skin moisture, tissue composition, anthropometric wrist variation (e.g., static variations in wrist position), and anthropometric wrist variation during gesture (e.g., dynamic variations in wrist positions). The performance characteristics based on these variety of factors are not well understood in the art, which can create a number of challenges in designing wearable devices that can accurately sense neuromuscular signals, while also ensuring that the device has a socially-acceptable form factor and can be built using a fewer number of component parts. Current designs of wearable devices for sensing neuromuscular signals can be large and bulky, often including a large number of sensors to detect neuromuscular signals (which creates a bulkier overall design for a wrist-wearable device). The large and bulky wearable devices can be uncomfortable to a user and can also make the devices less practical and less socially-acceptable for day-to-day use.

Additionally, some arrangements for sensing neuromuscular signals are configured to sense signals along a single direction (and can suppress or eliminate signal information along other directions). Thus, additional signal information can be lost.

As such, it would be desirable to provide wearable devices with a user-friendly (and aesthetically-pleasing, such as a less bulky) form factor for sensing neuromuscular signals, including by using only as many sensors as are needed to detect neuromuscular signals to enable accurate predictions of motor actions. It would also be desirable to design arrangements of sensors to ensure that additional signal information can also be recovered and used to enable more accurate (e.g., lower false positive and/or high true positive rates) and faster determinations as to the motor actions that a user is intending to perform.

SUMMARY

The wearable device for sensing neuromuscular signals described herein makes use of a shared reference electrode to, e.g., reduce the total number of electrodes in the wearable device, which allows for a lighter and more comfortable wearable device with a smaller-sized form factor and reduced overall cost. These improvements allow for the wearable device to be designed such that it is functional, practical, and socially acceptable for day-to-day use. Further, the wearable device for sensing neuromuscular signals described herein uses additional hardware improvements to detect radial information for neuromuscular signals (e.g., in addition to widthwise or longitudinal information sensed using electrodes positioned along a wearable structure, such as a watch band) from the data collected by one or more electrodes of the wearable device. In other words, the wearable devices described herein are capable of using a shared reference electrode, in addition to also (or alternatively) making use of neuromuscular signal information along more than one direction (e.g., widthwise and/or lengthwise placed electrodes).

Further, the wearable devices described herein can also improve users' interactions with artificial-reality environments and also improve user adoption of artificial-reality environments more generally by providing a form factor that is socially acceptable and compact, thereby allowing the user to wear the device throughout their day (and thus making it easier to interact with such environments in tandem with (as a complement to) everyday life). In the descriptions that follow, references are made to artificial-reality environments, which include, but are not limited to, virtual-reality (VR) environments (including non-immersive, semi-immersive, and fully-immersive VR environments), augmented-reality environments (including marker-based augmented-reality environments, markerless augmented-reality environments, location-based augmented-reality environments, and projection-based augmented-reality environments), hybrid reality, and other types of mixed-reality environments. As the skilled artisan will appreciate upon reading the descriptions provided herein, the novel wearable devices described herein can be used with any of these types of artificial-reality environments.

(A1) In accordance with some embodiments, an arm-wearable device for sensing neuromuscular signals using a shared reference electrode that is shared between two or more electrodes (e.g., other electrodes distinct from the reference electrode) is provided. The arm-wearable device includes a wearable structure configured to be worn by a user. The wearable structure has an interior surface and an exterior surface. The interior surface is configured to contact a user's skin when the arm-wearable device is donned by the user. The arm-wearable device further includes a first electrode at a first portion of the interior surface to form a first channel for detecting neuromuscular signals and a second electrode at a second portion, distinct from the first portion, of the interior surface to form a second channel for detecting neuromuscular signals. The arm-wearable device also includes a shared reference electrode at a third portion, distinct from the first and second portions, of the interior surface for detecting a reference neuromuscular signal that is compared to respective neuromuscular signals detected by the first electrode and the second electrode. A portion of each electrode of the first electrode, the second electrode, and the shared reference electrode contacts the user's skin above respective neuromuscular pathways of the user when the wearable structure is worn by the user. The arm-wearable device also includes circuitry configured to compare (i) the respective neuromuscular signals detected by the first electrode to the reference neuromuscular signal and (ii) the respective neuromuscular signals detected by the second electrode to the reference neuromuscular signal to allow for a determination by one or more processors of the arm-wearable device of a motor action that the user intends to perform with their hand.

(A2) In some embodiments of (A1), the shared reference electrode is only one shared reference electrode.

(A3) In some embodiments of any of (A1)-(A2), the shared reference electrode is configured to be positioned above an ulna bone of the user when the arm-wearable device is donned by the user.

(A3.5) In some embodiments of any of (A1)-(A2), the shared reference electrode is configured to be positioned above a center dorsal side of the user's wrist when the arm-wearable device is donned by the user.

(A4) In some embodiments of any of (A1)-(A3.5), the arm-wearable device further includes a ground electrode at a fourth portion of the interior surface distinct from the first, second, or third portions, the ground electrode configured to bias the circuitry.

(A5) In some embodiments of any of (A1)-(A4), the respective neuromuscular signals detected by the first electrode and the second electrode and the reference neuromuscular signal are detected along a same axis of the user's wrist.

(A5) In some embodiments of any of (A1)-(A4), the respective neuromuscular signals detected by the first electrode and the second electrode and the reference neuromuscular signal are detected along distinct axes of the user's wrist.

(A6) In some embodiments of any of (A1)-(A5.5), the reference neuromuscular signal is an unbuffered signal.

(A6.5) In some embodiments of any of (A1)-(A5.5), the reference neuromuscular signal is configured to be buffered before it is compared to the respective neuromuscular signals detected by the first electrode and the second electrode. The buffering of the reference neuromuscular signal is configured to reduce effects of noise and interference coupling in signals detected via the shared reference electrode.

(A7) In some embodiments of any of (A1)-(A6), the circuitry is configured use a first buffer to compare the respective neuromuscular signals detected by the first electrode to the reference neuromuscular signal, and the circuitry is configured to use a second buffer distinct from the first buffer to compare the respective neuromuscular signals detected by the second electrode to the reference neuromuscular signal.

(A7.5) In some embodiments of (A7), the first buffer is an instrumentation amplifier or a differential amplifier, and the second buffer is an instrumentation amplifier or a differential amplifier.

(A8) In some embodiments of any of (A1)-(A7.5), the first and second channels for detecting neuromuscular signals are part of at least two channels for sensing neuromuscular signals, each of the at least two channels including respective electrodes at a distinct position of the wearable structure, and the circuitry is configured to compare respective neuromuscular signals detected by the respective electrodes of each of the at least two channels to the reference neuromuscular signal to allow for the determination by one or more processors of the arm-wearable device of the motor action that the user intends to perform with their hand (A8.2) In some embodiments of (A8), the at least two channels include at least six channels.

(A8.5) In some embodiments of any of (A1)-(A7.5), the first and second channels for detecting neuromuscular signals are part of no more than fifteen (e.g., at least two, three, four, five, six, seven, or eight) channels for sensing neuromuscular signals, each of the no more than fifteen channels including respective electrodes at a distinct portion of the wearable structure. In some embodiments, the circuitry is further configured to compare respective neuromuscular signals detected by respective electrodes of each of the no more than fifteen channels to the reference neuromuscular signal to allow for the determination by one or more processors of the arm-wearable device of the motor action that the user intends to perform with their hand.

(A9) In some embodiments of (A8.5), the no more than fifteen channels include six channels.

(A10) In some embodiments of any of (A1)-(A9), the arm-wearable device further includes a shield electrode at a fifth portion of the interior surface distinct from the first, second, third, or fourth portions. A portion of the shield electrode is configured to contact the user's skin above respective neuromuscular pathways of the user when the wearable structure is worn by the user.

(A10.1) In some embodiments of any of (A1)-(A9), the arm-wearable device further includes one or more shield electrodes. Each shield electrode operating as a shield, is positioned at a distinct portion of the interior surface adjacent to respective one or more electrodes for sensing neuromuscular signals, and contacts the user's skin above respective neuromuscular pathways of the user when the wearable structure is worn by the user. Further, the one or more shield electrodes are configured to further reduce effects of noise and interference coupling in signals detected via the shared reference electrode.

(A10.3) In some embodiments of (A10.1), at least one shield electrode of the one or more shield electrodes is positioned at an adjacent channel relative to another shield electrode of the one or more shield electrodes.

(A10.5) In some embodiments of (A10.1), at least one shield electrode of the one or more shield electrodes is positioned such that adjacent channels do not include shield electrodes.

(A10.7) In some embodiments of any of (A10.1)-(A10.5), the one or more shield electrodes include at least four shield electrodes.

(A11) In some embodiments of any of (A1)-(A10.7), each electrode of the first electrode, the second electrode, and the shared reference electrode is a gold-plated electrode having a spherical cap shape with a radius of 5 mm. Alternatively, one of more of these electrodes can be a soft electrode made of, e.g., a conductive elastomer material.

(A12) In some embodiments of any of (A1)-(A11), each electrode of the first electrode, the second electrode, and the shared reference electrode extends beyond the interior surface of the wearable structure by a distance of at least 2 mm, such that when each respective electrode is depressed into the user's skin it reaches a skin-depression depth of at least 0.8 mm.

(A13) In some embodiments of any of (A1)-(A12), the motor action is associated with one or more input commands, and one or more processors of the arm-wearable device are further configured to provide the one or more input commands associated with the motor action to a computing device to cause the computing device to perform the one or more input commands in an artificial-reality environment.

(A14) In some embodiments of any of (A1)-(A13), the motor action is associated with one or more user interface control commands, and the arm-wearable device further includes a capsule including a display configured to present a user interface, and the one or more processors are further configured to cause the performance of the one or more user interface control commands in the user interface presented at the display based on the motor action.

(A15) In some embodiments of any of (A1)-(A14), the neuromuscular pathways include at least the muscles used for moving each of the user's digits and the user's wrist. When the arm-wearable device is donned on the user's arm or forearm the neuromuscular pathways include at least the muscles used for moving each of the user's digits, the user's wrist, and the user's forearm.

The portions at which different electrodes and a shield can be positioned can also be referred to, in some embodiments, as widthwise segments of an arm-wearable device, such that different electrodes can be positioned within different widthwise segments of an arm-wearable device. In such embodiments, electrodes within a certain widthwise segment can form a signal-sensing channel and sensed values can be compared to those from a shared reference electrode located elsewhere on the wrist-wearable device. In other embodiments, electrodes within one widthwise segment are understood to be at different positions of the wrist-wearable device and a single widthwise segment can be understood to create more than one signal-sensing channel (e.g. a first channel formed between a first electrode and the shared reference electrode and a second channel formed between a second electrode and the shared reference electrode).

(B1) In accordance with some embodiments, a method for sensing neuromuscular signals using a shared reference electrode that is shared between two or more electrodes is provided. The method is performed at an arm-wearable device including (i) a wearable structure configured to be worn by a user, the wearable structure having an interior surface and an exterior surface, (ii) a first electrode at a first portion of the interior surface to form a first channel, (iii) a second electrode at a second portion, distinct from the first portion, of the interior surface to form a second channel, (iv) a shared reference electrode aligned along a third portion, distinct from the first and second portions, of the interior surface, and (v) circuitry. The method includes contacting a user's skin with the interior surface when the arm-wearable device is donned by the user. Each electrode of the first electrode, the second electrode, and the shared reference electrode contacts the user's skin above respective neuromuscular pathways of the user when the wearable structure is worn by the user. The method further includes detecting, via the one or more first and second electrodes, neuromuscular signals from the respective neuromuscular pathways of the user and detecting, via the shared reference electrode, a reference neuromuscular signal that is compared to respective neuromuscular signals detected by the first electrode and the second electrode. The method further includes comparing, by the circuitry, (i) the respective neuromuscular signals detected by the first electrode to the reference neuromuscular signal and (ii) the respective neuromuscular signals detected by the second electrode to the reference neuromuscular signal to allow for a determination by one or more processors of the arm-wearable device of a motor action that the user intends to perform with their hand.

(B2) In some embodiments of (B1), the shared reference electrode is only one shared reference electrode.

(B3) In some embodiments of any of (B1)-(B2), the shared reference electrode is configured to be positioned above an ulna bone of the user when the arm-wearable device is donned by the user.

(B3.5) In some embodiments of any of (B1)-(B2), the shared reference electrode is configured to be positioned above a center dorsal side of the user's wrist when the arm-wearable device is donned by the user.

(B4) In some embodiments of any of (B1)-(B3.5), the arm-wearable device further includes a ground electrode at a fourth portion of the interior surface distinct from the first, second, or third portions. The ground electrode is configured to bias the circuitry.

(B5) In some embodiments of any of (B1)-(B4), the respective neuromuscular signals detected by the first electrode and the second electrode and the reference neuromuscular signal are detected along a same axis of the user's wrist.

(B5.5) In some embodiments of any of (B1)-(B4), the respective neuromuscular signals detected by the first electrode and the second electrode and the reference neuromuscular signal are detected along distinct axes of the user's wrist.

(B6) In some embodiments of any of (B1)-(B5.5), the reference neuromuscular signal is an unbuffered signal.

(B7) In some embodiments of any of (B1)-(B6), the reference neuromuscular signal is configured to be buffered before it is compared to the respective neuromuscular signals detected by the first electrode and the one or more second electrodes. Buffering of the reference neuromuscular signal is configured to reduce effects of noise and interference coupling into signals detected via the shared reference electrode.

(B8) In some embodiments of any of (B1)-(B7), the circuitry is configured to use a first buffer to compare the respective neuromuscular signals detected by the first electrode to the reference neuromuscular signal, and the circuitry is configured to use second buffer distinct from the first buffer to compare the respective neuromuscular signals detected by the second electrode to the reference neuromuscular signal.

(B8.5) In some embodiments of (B8), the first buffer is an instrumentation amplifier or a differential amplifier, and the second buffer is an instrumentation amplifier or a differential amplifier (B9) In some embodiments of any of (B1)-(B8.5), the arm-wearable device further includes a shield electrode at a fifth portion of the interior surface distinct from the first, second, third, or fourth portions. A portion of the shield electrode contacts the user's skin above respective neuromuscular pathways of the user when the wearable structure is worn by the user (B10) In some embodiments of any of (B1)-(B9), the motor action is associated with one or more input commands, and the method further includes providing, by the one or more processors, the one or more input commands associated with the motor action to a computing device to cause the computing device to perform the one or more input commands in an artificial-reality environment.

(B11) In some embodiments of any of (B1)-(B10), the motor action is associated with one or more user interface control commands, the arm-wearable device further includes a capsule including a display configured to present a user interface, and the method further includes causing, by the one or more processors, the performance of the one or more user interface control commands in the user interface presented at the display based on the motor action.

(B12) In some embodiments of any of (B1)-(B11), the neuromuscular pathways include the muscles used for moving each of the user's digits, the user's wrist, and/or the user's forearm.

(C1) In accordance with some embodiments, a method of manufacturing an arm-wearable device for sensing neuromuscular signals using a shared reference electrode between two or more electrodes is provided. The method includes providing a wearable structure configured to be worn by a user. The wearable structure having an interior surface and an exterior surface, the interior surface being configured to contact a user's skin when the arm-wearable device is donned by the user. The method further includes providing a first electrode at a first portion of the interior surface to form a first channel for detecting neuromuscular signals and providing a second electrode at a second portion, distinct from the first portion, of the interior surface to form a second channel for detecting neuromuscular signals. The method also includes providing a shared reference electrode at a third portion, distinct from the first and second portions, of the interior surface for detecting a reference neuromuscular signal that is compared to respective neuromuscular signals detected by the first electrode and the second electrode. Each electrode of the first electrode, the second electrode, and the shared reference electrode contacts the user's skin above respective neuromuscular pathways of the user when the wearable structure is worn by the user. The method also includes providing circuitry configured to compare (i) the respective neuromuscular signals detected by the first electrode to the reference neuromuscular signal and (ii) the respective neuromuscular signals detected by the second electrode data to the reference neuromuscular signal to allow for a determination by one or more processors of the arm-wearable device of a motor action that the user intends to perform with their hand.

(C2) In some embodiments of (C1), the method includes manufacturing the arm-wearable device such that it is further configured in accordance with any of the arm-wearable devices of (A2)-(A15).

(D1) In accordance with some embodiments, an arm-wearable device for determining motor actions to be performed based on neuromuscular signal differentials sensed along at least two different directions is provided. The arm-wearable device includes a wearable structure configured to be worn by a user. The wearable structure includes an interior surface and an exterior surface, the interior surface being configured to contact a user's skin when the arm-wearable device is donned by the user. The arm-wearable device also includes a predetermined number of channels, each channel formed by electrodes at respective portions of the interior surface and configured to detect neuromuscular signals. Each electrode contacts the user's skin above respective neuromuscular pathways of the user when the wearable structure is worn by the user. The arm-wearable device further includes one or more processors. The one or more processors are configured to determine a first plurality of signal differentials between respective neuromuscular signal values sensed by electrodes of each respective channel of the predetermined number of channels, each signal differential of the first plurality of signal differentials providing intra-channel information concerning neuromuscular activity in a widthwise direction of the interior surface of the wearable structure. The one or more processors are also configured to determine, for each channel of the predetermined number of channels, a signal average based on the respective neuromuscular signal values sensed by electrodes of a respective channel of the predetermined number of channels. The one or more processors are configured to determine a second plurality of signal differentials by comparing respective signal averages between different channels of the predetermined number of channels, each signal differential of the second plurality of signal differentials providing inter-channel information concerning neuromuscular activity in a radial direction around the user's wrist that is substantially perpendicular to the widthwise direction. The one or more processors are further configured to determine a motor action that the user intends to perform with their hand based on the intra-channel and inter-channel information.

(D2) In some embodiments of (D1), each signal differential of the first and second pluralities of signal differentials is a voltage differential. Alternatively, or additionally, in some embodiments, the signal differential is a differential between two different sensed neuromuscular signal values or difference between at least one characteristic of a neuromuscular signal sensed at two different positions along the wearable structure's length (e.g., "L," two distinct positions along an interior surface of the arm-wearable device, which can be in one example two distinct widthwise segments 245 and 246 in FIG. 2A).

(D3) In some embodiments of any of (D1)-(D2), determining a motor action that the user intends to perform with their hand includes determining a sensing direction. More specifically, determining the direction in which the senses (e.g., user moving their arm left can result in determining a signal related to left arm movement).

(D4) In some embodiments of any of (D1)-(D3), the one or more processors are further configured to determine signal noise between the first plurality of signal differentials and the second plurality of signal differentials, and cause the arm-wearable device to provide a mitigating signal to reduce the signal noise.

(D5) In some embodiments of (D4), the mitigating signal is an anti-phase signal directed towards the user's wrist to reduce signal noise.

(D6) In some embodiments of any of (D1)-(D5), each respective signal average based on respective neuromuscular signal values sensed by electrodes of a respective channel of the predetermined number of channels is an average voltage measured with respect to ground.

(D7) In some embodiments of any of (D1)-(D6), each electrode is a gold-plated electrode having a spherical cap shape with a radius of 5 mm. Alternative embodiments can also make use of soft electrodes which can be made of, e.g., a conductive elastomer material.

(D8) In some embodiments of any of (D1)-(D7), each electrode extends beyond the interior surface of the wearable structure by a distance of at least 2 mm, such that when each electrode is depressed into the user's skin it reaches a skin-depression depth of at least 0.8 mm.

(D9) In some embodiments of any of (D1)-(D8), the motor action is associated with one or more input commands, and the one or more processors are further configured to provide the one or more input commands associated with the motor action to a computing device to cause the computing device to perform the one or more input commands in an artificial-reality environment.

(D10) In some embodiments of any of (D1)-(D9), the motor action is associated with one or more user interface control commands, and the arm-wearable device further includes a capsule including a display configured to present a user interface. The one or more processors are further configured to cause the performance of the one or more user interface control commands in the user interface presented at the display based on the motor action.

(D11) In some embodiments of any of (D1)-(D10), the neuromuscular pathways include at least the muscles used for moving each of the user's digits and the user's wrist. When the arm-wearable device is donned on the user's arm or forearm the neuromuscular pathways include at least the muscles used for moving each of the user's digits, the user's wrist, and the user's forearm.

(E1) In accordance with some embodiments, a method for determining motor actions to be performed based on neuromuscular signal differentials sensed along at least two different directions is provided. The method is performed at an arm-wearable device including (i) a wearable structure configured to be worn by a user, the wearable structure having an interior surface and an exterior surface, (ii) a predetermined number of channels, each channel formed by electrodes aligned along respective portions of the interior surface, and (iii) one or more processors. The method includes contacting a user's skin with the interior surface when the arm-wearable device is donned by the user. Each electrode contacts the user's skin above respective neuromuscular pathways of the user when the wearable structure is worn by the user. The method also includes detecting, via the predetermined number of channels, neuromuscular signals from the respective neuromuscular pathways of the user. The method includes determining a first plurality of signal differentials between respective neuromuscular signal values sensed by electrodes of each respective channel of the predetermined number of channels. Each signal differential of the first plurality of signal differentials provides intra-channel information concerning neuromuscular activity in a widthwise direction of the interior surface of the wearable structure. The method further includes determining, for each channel of the predetermined number of channels, a signal average based on the respective neuromuscular signal values sensed by electrodes of a respective channel of the predetermined number of channels. The method includes determining a second plurality of signal differentials by comparing respective signal averages between different channels of the predetermined number of channels. Each signal differential of the second plurality of signal differentials provides inter-channel information concerning neuromuscular activity in a radial direction around the user's wrist that is substantially perpendicular to the widthwise direction. The method includes determining a motor action that the user intends to perform with their hand based on the intra-channel and inter-channel information.

(E2) In some embodiments of (E1), each signal differential of the first and second pluralities of signal differentials is a voltage differential. Alternatively, or additionally, in some embodiments, the signal differential is a differential between two different sensed neuromuscular signal values or difference between at least one characteristic of a neuromuscular signal sensed at two different positions along the wearable structure's length.

(E3) In some embodiments of any of (E1)-(E2), determining a motor action that the user intends to perform with their hand includes determining a sensing direction.

(E4) In some embodiments of any of (E1)-(E3), the method includes determining, via the one or more processors, signal noise between the first plurality of signal differentials and the second plurality of signal differentials, and causing the arm-wearable device to provide a mitigating signal to reduce the signal noise.

(E5) In some embodiments of (E4), the mitigating signal is an anti-phase signal directed towards the user's wrist to reduce signal noise.

(E6) In some embodiments of any of (E1)-(E5), each respective signal average based on respective neuromuscular signal values sensed by electrodes of a respective channel of the predetermined number of channels is an average voltage measured with respect to ground.

(E7) In some embodiments of any of (E1)-(E6), each electrode is a gold-plated electrode having a spherical cap shape with a radius of 5 mm.

(E8) In some embodiments of any of (E1)-(E7), each electrode extends beyond the interior surface of the wearable structure by a distance of at least 2 mm, such that when each electrode is depressed into the user's skin it reaches a skin-depression depth of at least 0.8 mm.

(E9) In some embodiments of any of (E1)-(E8), the motor action is associated with one or more input commands, and the method further includes providing, via the one or more processors, the one or more input commands associated with the motor action to a computing device to cause the computing device to perform the one or more input commands in an artificial-reality environment.

(E10) In some embodiments of any of (E1)-(E9), the motor action is associated with one or more user interface control commands, and the arm-wearable device includes a capsule including a display configured to present a user interface. The method further includes causing, via the one or more processors, the performance of the one or more user interface control commands in the user interface presented at the display based on the motor action.

(E11) In some embodiments of any of (E1)-(E10), the neuromuscular pathways include the muscles used for moving each of the user's digits, the user's wrist, and/or the user's forearm.

(F1) In accordance with some embodiments, a method of manufacturing an arm-wearable device for determining motor actions to be performed based on neuromuscular signal differentials sensed along at least two different directions is provided. The method includes providing a wearable structure configured to be worn by a user. The wearable structure includes an interior surface and an exterior surface, the interior surface being configured to contact a user's skin when the arm-wearable device is donned by the user. The method includes providing a predetermined number of channels, each channel formed by electrodes aligned along respective portions of the interior surface and configured to detect neuromuscular signals. Each electrode contacts the user's skin above respective neuromuscular pathways of the user when the wearable structure is worn by the user. The method further includes providing one or more processors. The one or more processors are configured to determine a first plurality of signal differentials between respective neuromuscular signal values sensed by electrodes of each respective channel of the predetermined number of channels. Each signal differential of the first plurality of signal differentials provides intra-channel information concerning neuromuscular activity in a widthwise direction of the interior surface of the wearable structure. The one or more processors are also configured to determine, for each channel of the predetermined number of channels, a signal average based on the respective neuromuscular signal values sensed by electrodes of a respective channel of the predetermined number of channels. The one or more processors are configured to determine a second plurality of signal differentials by comparing respective signal averages between different channels of the predetermined number of channels, each signal differential of the second plurality of signal differentials providing inter-channel information concerning neuromuscular activity in a radial direction around the user's wrist that is substantially perpendicular to the widthwise direction. The one or more processors are further configured to determine a motor action that the user intends to perform with their hand based on the intra-channel and inter-channel information.

(F2) In some embodiments of (F1), the method includes manufacturing the arm-wearable device such that it is further configured in accordance with any of the arm-wearable devices of (D2)-(D11).

(G1) In accordance with some embodiments, an arm-wearable device for sensing neuromuscular signals using a shared reference electrode that is shared between two or more electrodes is provided. The arm-wearable device includes a wearable structure configured to be worn by a user. The wearable structure has an interior surface and an exterior surface. The interior surface is configured to contact a user's skin when the arm-wearable device is donned by the user. The arm-wearable device further includes a first electrode at a first portion of the interior surface for detecting neuromuscular signals and a second electrode at a second portion, distinct from the first portion, of the interior surface for detecting neuromuscular signals. The arm-wearable device also includes a shared reference electrode at a third portion, distinct from the first and second portions, of the interior surface for detecting a reference neuromuscular signal that is compared to respective neuromuscular signals detected by the first electrode and the second electrode. A portion of each electrode of the first electrode, the second electrode, and the shared reference electrode contacts the user's skin above respective neuromuscular pathways of the user when the wearable structure is worn by the user. The arm-wearable device also includes circuitry configured to compare (i) the respective neuromuscular signals detected by the first electrode to the reference neuromuscular signal and (ii) the respective neuromuscular signals detected by the second electrode to the reference neuromuscular signal to allow for a determination by one or more processors of the arm-wearable device of a motor action that the user intends to perform with their hand.

(G2) In some embodiments of (G1), the arm-wearable device is further configured in accordance with any of the arm-wearable devices of (A2)-(A15).

(H1) In accordance with some embodiments, an arm-wearable device for determining motor actions to be performed based on neuromuscular signal differentials sensed along at least two different directions is provided. The arm-wearable device includes a wearable structure configured to be worn by a user. The wearable structure includes an interior surface and an exterior surface, the interior surface being configured to contact a user's skin when the arm-wearable device is donned by the user. The arm-wearable device also includes a predetermined number of electrodes at respective portions of the interior surface and configured to detect neuromuscular signals. Each electrode contacts the user's skin above respective neuromuscular pathways of the user when the wearable structure is worn by the user. The arm-wearable device further includes one or more processors. The one or more processors are configured to determine a first plurality of signal differentials between respective neuromuscular signal values sensed by adjacent electrodes of the predetermined number of electrodes in a first direction (e.g., positive and negative electrodes of FIG. 6), each signal differential of the first plurality of signal differentials providing first directional electrode information (e.g., intra-electrode information) concerning neuromuscular activity in a widthwise direction of the interior surface of the wearable structure. The one or more processors are also configured to determine, for each set of electrodes of the predetermined number of electrodes in a second direction distinct from the first direction (e.g., channels 0 through channel N of FIG. 6), a signal average based on the respective neuromuscular signal values sensed by electrodes of a respective set of electrodes of the predetermined number of electrodes in the second direction. The one or more processors are configured to determine a second plurality of signal differentials by comparing respective signal averages between different set of electrodes of the predetermined number of electrodes in the second direction, each signal differential of the second plurality of signal differentials providing second directional electrode information (e.g., inter-electrode information) concerning neuromuscular activity in a radial direction around the user's wrist that is substantially perpendicular to the widthwise direction. The one or more processors are further configured to determine a motor action that the user intends to perform with their hand based on the first directional electrode information and second directional electrode information.

(H2) In some embodiments of (H1), the arm-wearable device is further configured in accordance with any of the arm-wearable devices of (D2)-(D11).

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

So that the present disclosure can be understood in greater detail, a more particular description may be had by reference to the features of various embodiments, some of which are illustrated in the appended drawings. The appended drawings, however, merely illustrate pertinent features of the present disclosure and are therefore not to be considered limiting, for the description may admit to other effective features as the person of skill in this art will appreciate upon reading this disclosure.

FIGS. 2A-2D illustrate first and second embodiments of an arm-wearable device for sensing neuromuscular signals, in accordance with some embodiments.

FIG. 10 shows a detailed flow diagram of a method for sensing neuromuscular signals using a shared reference electrode of an arm-wearable device, according to some embodiments.

FIGS. 11A and 11B are flow diagrams illustrating a method of manufacturing an arm-wearable device for sensing neuromuscular signals using a shared reference electrode, in accordance with some embodiments.

FIGS. 12A and 12B show detailed flow diagrams of a method for sensing neuromuscular signals along a radial direction (e.g., in addition to a widthwise direction) using one or more channels of an arm-wearable device, according to some embodiments.

FIGS. 13A and 13B are flow diagrams illustrating a method of manufacturing an arm-wearable device for sensing neuromuscular signals along a radial direction using one or more channels, in accordance with some embodiments.

Figure 1A:
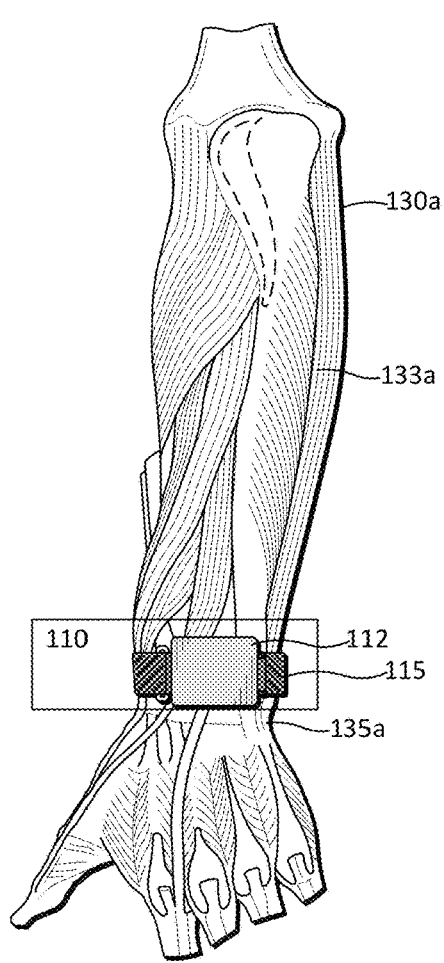
FIGS. 1A-1C illustrate a wearable device 110 (e.g., an arm-wearable device) for sensing neuromuscular signals using one or more electrodes, in accordance with some embodiments

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method, or device. Finally, like reference numerals may be used to denote like features throughout the specification and figures.

DETAILED DESCRIPTION

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not been described in exhaustive detail so as not to unnecessarily obscure pertinent aspects of the embodiments described herein.

Figure 1B:
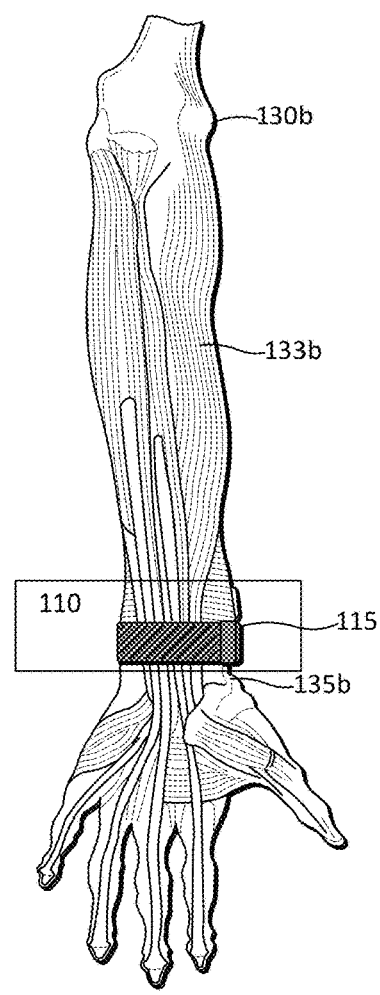
Figure 1C:
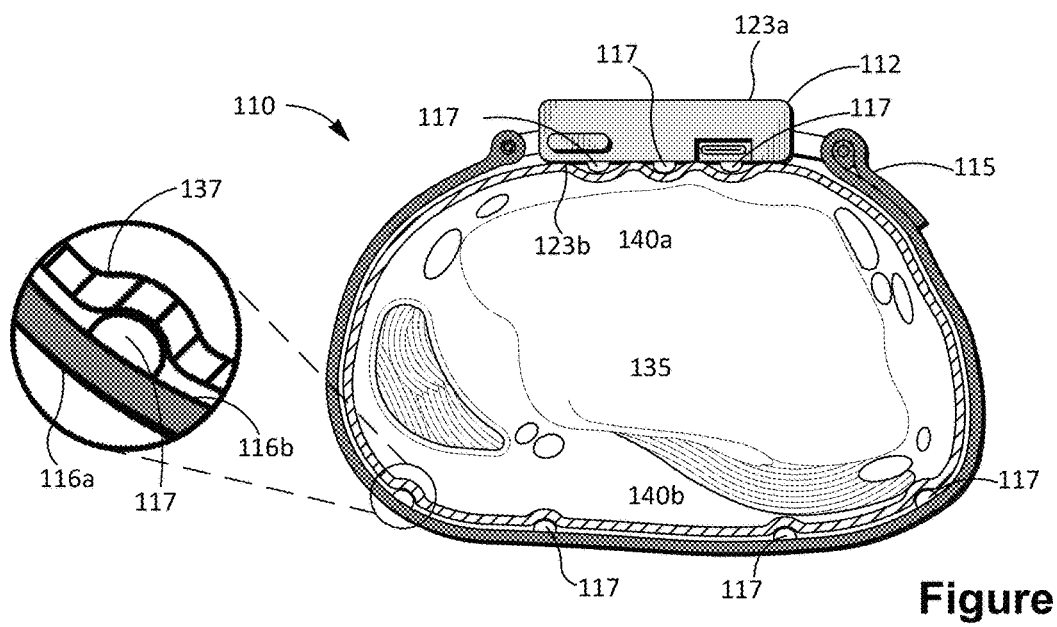

FIGS. 1A-1C illustrate a wearable device 110 (e.g., an arm-wearable device) for sensing neuromuscular signals using one or more electrodes, in accordance with some embodiments. The wearable device 110 includes a wearable structure (which can include a band portion 115, a capsule portion 112, and a cradle portion (shown and described in detail below in reference to FIGS. 14A and 14B) that is coupled with the band to allow for the capsule portion 112 to be removably coupled with the band portion 115) configured to be worn by a user. For embodiments in which the capsule portion 112 is removable, the capsule portion 112 is referred to as a removable structure, such that in these embodiments the wearable device 110 includes a wearable portion (band portion and the cradle portion) and a removable structure (the removable capsule portion which can be removed from the cradle). The wearable device 110 includes one or more processors (e.g., CPU 1526, MCU 1552, etc.; FIG. 15). The one or more processors are included in the wearable structure (e.g., a computing core, the capsule portion 112, the band portion 115, the capsule portion 112, and/or the cradle portion). In some embodiments, the interior surface of the wearable structure 110 includes one or more electrodes 117 configured to detect neuromuscular signals (as described below in reference to FIG. 1C). The one or more components of the wearable device 110 are discussed below.

The wearable structure 110 includes an interior surface (interior surfaces 205; FIG. 2) and an exterior surface. In some embodiments, the interior surface includes an interior band surface 116b, as well as an interior capsule surface 123b of the capsule portion. In some embodiments, the exterior surface includes an exterior band surface 116a, as well as an exterior capsule surface 123a of the capsule portion. The interior surface is configured to contact a user's skin 137 when the wearable device 110 is donned by the user (e.g., on user's arm as shown in dorsal arm view 130a and ventral arm view 130b of FIGS. 1A and 1B). In some embodiments, the wearable structure is configured to wrap around a user's wrist 135 (e.g., dorsal wrist portion 135a and ventral wrist portion 135b as shown in FIGS. 1A and 1B). The wearable structure wraps around a user's wrist 135 such that the one or more electrodes 117 contact the user's skin 137 above respective neuromuscular pathways of the user as described below.

In some embodiments, the capsule 112 houses the one or more processors (e.g., CPU 1526). The capsule 112 can be a component part of the wearable structure (as noted above). The capsule portion 112 is configured to be positioned on top of the user's wrist 135 or forearm 133 (or at any position along their arm) when the user dons or wears the wearable structure (with the band portion 115 surround a remainder of the user's wrist). In some embodiments, the capsule 112 includes a display (display screen 1415; FIG. 14) configured to present a user interface. In some implementations, the user interface includes one or more applications (or "apps"), such as a clock, a calendar, a calculator, social media platforms, games, an email client, a browser, and/or other productivity and/or entertainment applications. Alternatively, in some embodiments, the capsule 112 does not include a display (and is used to house and protect the one or more processors as well as other components of the wearable device 110 discussed below in reference to FIG. 15). In some embodiments, the capsule 112 includes one or more electrodes 117 such that when the capsule 112 is coupled to the wearable structure (either directly or by way of a removable connection to a cradle portion of the wearable structure), the one or more electrodes 117 of the capsule 112 operate in conjunction with electrodes 117 of a band portion 115 of the wearable structure. The one or more electrodes 117 of the capsule 112 contact the user's skin 137 above respective neuromuscular pathways of the user as described below.

Turning to FIG. 1C, the one or more electrodes are aligned along different portions of the interior surface 116b to form respective channels for detecting neuromuscular signals. In some embodiments, the one or more electrodes 117 include a ground (e.g., ground electrode 230; FIGS. 2A-2D) and/or a shield (e.g., shield electrode 240; FIGS. 2A-2D).

In some embodiments, each electrode 117 is a gold-plated electrode. In some embodiments, the electrodes include a hard gold plating, which is gold alloyed with cobalt, iron, or nickel for durability. Alternatively, in some embodiments, the electrodes include a soft gold plating, which is gold with high purity (e.g., 99% gold purity) without the addition of any alloying elements. The electrodes are formed such that there is a high percentage of gold (e.g. at least 80 percent) at the electrode-skin interface. Other embodiments can use electrodes formed of a conductive elastomer material.

In some embodiments, the one or more electrodes 117, which can be soft electrodes made of a conductive elastomer, are embedded within the band portion 115 and/or the capsule 112 such that they are flush with the band portion 115 and/or the capsule 112 (i.e., do not extend beyond the interior band surface 116b and the interior capsule surface 123b). The one or more electrodes 117 are configured to contact the user's skin 137 above respective neuromuscular pathways of the user when the wearable structure is worn by the user. Alternatively, in some embodiments, the one or more electrodes 117 have a spherical cap shape. In some embodiments, the spherical cap shape has a radius of at least 5 mm. The one or more electrodes 117 can include different shapes (e.g., squares, triangles, flat contacts, or other surfaces that touch a user's skin 137) and different dimensions (e.g., surface areas, widths, radius, etc.). Each electrode 117 extends beyond the interior surface of the wearable structure by a distance of at least 2 mm, such that when the wearable device 110 is donned by the user, each electrode 117 is depressed into the user's skin 137 to reach a skin-depression depth of at least 0.8 mm. For purposes of this disclosure, a skin-depression depth is defined as a distance between a point on the user's skin 137 when that skin is not being depressed and the same point on the user's skin 137 when that skin 137 is being pushed down (e.g., depressed) by the portion of the area of an electrode 117. For example, as shown in FIG. 1C, portions of the wearable structure not including an electrode 117 do not cause a visible skin-depression depth on the user's skin 137 as the user's skin 137 has not been depressed by an electrode 117. The one or more electrodes 117 are designed such that vertical movement does not significantly change the contact surface area throughout the tissue indentation (i.e., the skin-depression depth). The dimensions of the one or more electrodes 117 result in electrode skin contact areas that provide stable and reliable sensing of neuromuscular signals travelling through the neuromuscular pathways within the user's wrist or forearm while remaining comfortable to users. The above dimensions of the one or more electrodes 117 are non-limiting, the skilled artisan in this field will appreciate upon reading this disclosure that different electrode lengths, radiuses, width, areas, electrode shapes, etc. can be used to achieve the electrode skin contact areas.

In some embodiments, respective channels are formed, in part, by each electrode aligned along the interior surface 116b and a shared reference electrode. More specifically, the shared reference electrode allows for a channel to be formed in part by a single electrode aligned along a distinct portion of the interior surface 116b whose sensed neuromuscular signals are compared with reference neuromuscular signal sensed by the shared reference electrode. Alternatively, some systems utilize pairs of electrodes aligned along distinct widthwise segments of the interior surface 116b to form respective channels (e.g., these systems use at least two electrodes for sensing neuromuscular signals at a widthwise segment to form a channel). In some embodiments, at least two channels for detecting neuromuscular signals are formed, in part, by the one or more electrodes 117. In some embodiments, at least four channels for detecting neuromuscular signals are formed, in part, by the one or more electrodes 117. In some embodiments, at least five channels for detecting neuromuscular signals are formed, in part, by the one or more electrodes 117. In some embodiments, at least fifteen channels for detecting neuromuscular signals are formed, in part, by the one or more electrodes. The above examples are non-limiting—any number of channels can be formed, in part, by the one or more electrodes 117. Additional examples of different configurations and alignments of the one or more electrodes 117 are provided below in reference to FIGS. 2A-2D. The one or more electrodes 117 that form respective channels are disposed over one or more neuromuscular pathways. The one or more electrodes 117 detect neuromuscular signals that travel through the neuromuscular pathways (e.g., first set of neuromuscular pathways 140a and second set of neuromuscular pathways 140b discussed below) within the user's wrist 135 (e.g., dorsal wrist portion 135a and ventral wrist portion 135b) or forearm 135 (e.g., dorsal forearm portion 133a and ventral forearm portion 133b).

The first set of neuromuscular pathways 140a and second set of neuromuscular pathways 140b include muscles (e.g., extensors and/or flexors) used for moving each of the user's digits. In some embodiments, the first set of neuromuscular pathways 140a and second set of neuromuscular pathways 140b provide neuromuscular signals for detecting hand movement, movement of one or more digits, gestures (e.g., pinch gestures in which one digit contacts another digit, clenching a hand (or forming a fist), etc.). In some embodiments, first set of neuromuscular pathways 140a and second set of neuromuscular pathways 140b include neuromuscular pathways of the user's wrist 135 including extensors and flexors for the index and the middle digits. In some embodiments, the first set of neuromuscular pathways 140a are at a dorsal portion of the hand and/or wrist (e.g., upper portion of the hand) and are used to monitor extensor muscles. In some embodiments, the second set of neuromuscular pathways 140b are at a palmar portion of the hand and/or wrist (e.g., palm portion of the hand) and are used to monitor flexor muscles. In some embodiments, the first set of neuromuscular pathways 140a and the second set of neuromuscular pathways 140b allow for crosstalk such that a substantial number of extensor and flexor muscles are detectable.

For example, the first set of neuromuscular pathways 140a and/or second set of neuromuscular pathways 140b can allow for the detection of neuromuscular signals from one or more extensor muscles including one or more of extensor digiti minimi (which extends a pinky finger), extensor digitorum communis (which extends the medial four digits), extensor indicis (which extends an index finger), extensor pollicis longus (which extends a thumb), extensor carpi radialis (which extends a wrist in radial direction), and extensor carpi ulnaris (extends the wrist in ulnar direction). In another example, the first set of neuromuscular pathways 140a and/or second set of neuromuscular pathways 140b can allow for the detection of neuromuscular signals from one or more flexor muscles including one or more of the flexor digitorum *profundus* (a muscle in the forearm of humans that flexes the digits), the flexor carpi radialis muscle (a muscle of the human forearm that acts to flex and (radially) abduct the hand), flexor carpi ulnaris muscle (a muscle of the forearm that flexes and adducts at the wrist joint), flexor Pollicis *Brevis* Muscle (a muscle in the hand that flexes the thumb), flexor digiti minimi *Brevis* Muscle of Hand (a hypothenar muscle in the hand that flexes the little digit (or pinkie digit) at the metacarpophalangeal joint), pronator quadratus (which controls roll movement of the wrist), flexor retinaculum of the hand (the roof of the carpal tunnel, through which the median nerve and tendons of muscles which flex the hand pass), the flexor digitorum superficialis muscle (whose primary function is flexion of the middle phalanges of the four digits (excluding the thumb) at the proximal interphalangeal joints, however under continued action it also flexes the metacarpophalangeal joints and wrist joint), and palmaris longus (which is not present in all humans).

The one or more processors (e.g., CPU 1526 and/or MCU 1552) are configured to receive data about the neuromuscular signals (e.g., detected by the one or more electrodes 117) to determine a motor action that the user intends to perform with their hand. In some embodiments, the one or more processors receive data about the neuromuscular signals and a reference neuromuscular signal (detected from a shared reference electrode 217; FIGS. 2A-2D) to determine a motor action that the user intends to perform with their hand. In some embodiments, the neuromuscular signals and the reference neuromuscular signal detected by the one or more electrodes 117 are detected along the same axis of the user's wrist 135. In some embodiments, the one or more processors compare the neuromuscular signals detected by the one or more electrodes to the reference neuromuscular signal to allow for a determination by one or more processors of the arm-wearable device 110 of a motor action that the user intends to perform with their hand. In some embodiments, as discussed below in reference to FIGS. 6-8B, the one or more processors use the received data about the neuromuscular signals to determine signal differentials and/or signal averages, which are used to determine a motor action that the user intends to perform with their hand. For example, in some embodiments, the one or more processors determine a motor action that the user intends to perform with their hand based on intra-channel and inter-channel neuromuscular-signal information (e.g., in other words, motor actions are more accurately and more quickly determined using neuromuscular-signal information from two different signal-sensing directions).

In some embodiments, the motor action is associated with one or more input commands, and the one or more processors are configured provide the one or more input commands associated with the motor action to a computing device to cause the computing device to perform the one or more input commands in an artificial-reality environment (e.g., augmented reality (AR) or virtual reality (VR) environment). For example, the determined motor action can be interpreted by the one or more processors as a gesture for causing performance of an action within (i) a display that is coupled with the exterior surface (e.g., as a part of the capsule 112) of the wearable structure and/or an artificial-reality environment being presented via a head-mounted display (or other computing device, such as a computer) that is separate from the wearable device 110. Alternatively, in some embodiments, the one or more processors are configured provide the motor action directly to a computing device to cause the computing device to perform the one or more input commands associated with the motor action. In other words, the computing device receives the motor action and interprets it as being associated with one or more input commands that are then caused to be executed at the computing device.

In some embodiments, the motor action is associated with one or more interface control commands, and the one or more processors are further configured to cause the performance of the one or more user interface control commands. For example, the wearable device 110 can include a capsule 112 that includes a display configured to present a user interface and, based on a determined motor action, the one or more processors cause one or more actions to be performed on the user interface (e.g., selecting a menu option presented within the user interface). In another example mentioned in the preceding paragraph, the one or more processors can be communicatively coupled (via a communication interface, such as LTE 1518, WIFI/Bluetooth 1520, etc.; FIG. 15) to a remote computing device (e.g., a phone, a computer, smart glasses, etc.) and the one or more the one or more processors cause one or more actions to be performed on the user interface of the remote computing device.

While some of the examples discussed herein refer to the capsule portion 112 including a certain number of electrodes (e.g., one or more neuromuscular-signal-sensing electrodes, a ground electrodes, and a shield electrode) and the band portion 115 also include a certain number of electrodes (e.g., one or more neuromuscular-signal-sensing electrodes), one of skill in this art will appreciate that this example arrangement could be altered such that some of the one or more electrodes on the capsule portion 112 are coupled with a cradle portion of the wearable structure instead (such that all or a portion of the one or more electrodes are on the capsule and a remainder (or no) electrodes are coupled to the capsule). Similarly, the positions of the one or more electrodes 117 shown in FIG. 1C are non-limiting and can be rearranged to receive the desired data about the neuromuscular signals. Different examples of the positions of the one or more electrodes 117 are provided below in reference to FIGS. 2A-2D.

FIGS. 2A-2D illustrate different embodiments of an arm-wearable device for sensing neuromuscular signals, in accordance with some embodiments. FIG. 2A-2D shows different configurations of the arm-wearable device. Each configuration of the arm-wearable device illustrates a bottom view of the arm-wearable device including an interior surface 205, a capsule 112, a first electrode 215 for detecting neuromuscular signals, a second electrode 216 for detecting neuromuscular signals, a shared reference electrode 217, a plurality of shorted reference nodes 219, a ground electrode 230, one or more shield electrodes 240 in different configurations. Each of the first electrode 215, the second electrode 216, the shared reference electrode 217, the ground electrode 230, and the one or more shield electrodes 240 are at a portion of the interior surface 205 of the arm-wearable device (e.g., an interior band surface 116b and an interior capsule surface 123b; FIG. 1).

In some embodiments, the shared reference electrode 217 is used to form the plurality of shorted reference nodes 219. The shared reference electrode 217 is shorted such that the reference neuromuscular signal is in the same plane as the one or more first electrodes 215 and the one or more second electrodes 216. For ease of discussion, each shorted electrode of the plurality of shorted reference nodes 219 is shown as an electrode; however, the plurality of shorted reference nodes 219 are not exposed and do not extend beyond the interior surface 205 (i.e., the plurality of shorted reference nodes 219 can be within or internal to the interior surface 205). Because the plurality of shorted reference nodes 219 are not exposed, power line interference that can be introduced is minimized or eliminated for the first embodiment of the arm-wearable device 200 or the second embodiment of the arm-wearable device 250. In some embodiments, the plurality of shorted reference nodes 219 can be at any portion of the interior surface 205.

A single electrode for sensing neuromuscular signals, when used with the shared reference electrode 217, forms a part of a channel (another part can be the shared reference electrode to allow for differential sensing). For example, the first electrode 215 and the second electrode 216 each form a respective channel when used in conjunction with the shared reference electrode 217. An arm-wearable device configuration can include one or more channels. In some embodiments, the one or more channels of arm-wearable device can be positioned on the same axis or the distinct axes. The different configurations of the arm-wearable devices shown in FIGS. 2A-2D illustrate non-exhaustive examples of arm-wearable devices with predetermined channels of electrodes (e.g., at least four channels, at least five channels, at least 15 channels, etc.).

For ease, FIG. 2A-2D reference a first electrode 215 and a second electrode 216; however, it should be appreciated that the arm-wearable device can include more than two electrodes for detecting neuromuscular signals (e.g., as shown by the additional electrodes with a diagonal line pattern). As discussed below, in some embodiments, more than one electrode (e.g., first and/or second electrodes 215 and 216) can be positioned at different portions of the of the interior surface 205 of the arm-wearable device. The plurality of shorted reference nodes 219 are shown in dotted lines to represent electrodes that have been removed from the arm-wearable device. As described above, the plurality of shorted reference nodes 219 are not physical electrodes that contact the user's skin, rather the plurality of shorted reference nodes 219 represent circuitry that is shorted with the shared reference electrode 217. Portions of the arm-wearable device showing the plurality of shorted reference nodes 219 would be covered by a band portion of the arm-wearable device. Similarly, empty spaces 243 shown as electrodes with dotted lines represent different positions along an arm-wearable device in which one or more electrodes can be positioned. For example, the first electrode 215, the second electrode 216, the shared reference electrode 217, the ground electrode 230, the one or more shielding electrodes 240, and/or other electrodes can be positioned along the different portions shown by empty spaces 243. It should be noted that empty spaces 243 are not exposed. More specifically, if an electrode is not located at one of the empty spaces 243, a portion of the band would then cover the empty space 243.

Turning to FIG. 2A, a first embodiment of the arm-wearable device 200 shows the first electrode 215 aligned along a first widthwise segment 245 of the interior surface 205 and the second electrode 216 at a second widthwise segment 246, distinct from the first widthwise segment 245, of the interior surface 205. When combined with the shared reference electrode 217, the first electrode 215 forms, in part, a first channel for detecting neuromuscular signals (from respective neuromuscular pathways of the user as described above in reference to FIGS. 1A-1C) and the second electrode 216 forms, in part, a second channel for detecting neuromuscular signals. In some embodiments, the first and second channels for detecting neuromuscular signals are part of at least fifteen channels for sensing neuromuscular signals. In some embodiments, one or more additional electrodes for sensing neuromuscular signals can be positioned within a respective widthwise segments of the interior surface 205 (or any position along the interior surface 205 of the arm-wearable device 210). Each additional electrode, when combined with the shared reference electrode 217, forms a respective channel. For example, the first widthwise segment 245 can include the first electrode 215 and/or one or more additional electrodes (aligned at any position within the first widthwise segment 245), each electrode forming a channel when combined with the shared reference electrode 217. In other words, use of the shared reference electrode 217, provides greater design flexibility by reducing the number of electrodes needed to form a respective channel. As an example, a system including at least fifteen channels would include two or more electrodes aligned along a distinct widthwise segment of the wearable structure (e.g., this is represented by the removed electrodes shown in FIG. 2A).

Although the first and second electrodes 215 and 216 are shown and described as positioned at respective widthwise segments, one of skill in this art will appreciate that this example arrangement could be altered such that the electrodes can be placed along different portions of the interior surface 205 of the arm-wearable device 210. For example, the first and second electrodes 215 and 216 (as well as any additional electrodes) can be positioned at any of the empty spaces 243, the location of the plurality of shorted reference nodes 219, the interior capsule surface 123b of the capsule 112, and/or any other position along the interior surface 205 of the arm-wearable device 210. Further, the first and second electrodes 215 and 216 (or any other electrode) are not required to be positioned in widthwise segments.

It should also be appreciated that the use of a shared reference electrode can allow for dynamically defined sensing channels. For instance, a default configuration of channels can be employed and then that default configuration can be modified at various points in time to change the channel definitions (e.g., a first electrode and a shared reference electrode might form a channel at one point in time and, then, based on a determination that this channel definition is not effective enough at detecting neuromuscular signals associated with certain muscle groups, then channel definition can be modified such that the first electrode is replaced or supplemented as part of this particular channel definition (e.g., a different electrode can become part of this channel as a replacement to, or a supplement for, the first electrode)).

In some embodiments, the shared reference electrode 217 is aligned along a third widthwise segment 247, distinct from the first and the second widthwise segments 245 and 246, of the interior surface 205 and detects a reference neuromuscular signal. The shared reference electrode 217 can be positioned without any adjacent electrodes (e.g., no other electrodes are positionally adjacent in a certain widthwise segment of the interior surface 205). Alternatively, the shared reference electrode 217 can be adjacent to a first electrode 215, a second electrodes 216, a ground electrode 230, and/or a shield electrode 240. The shared reference electrode 217 is a single electrode configured to contact a portion of the user's skin. In some embodiments, the shared reference electrode 217 is configured to be positioned above an ulna bone of the user when the arm-wearable device is donned by the user. In some embodiments, the shared reference electrode 217 is configured to be positioned above a center dorsal side of the user's wrist when the arm-wearable device is donned by the user. The above examples of the position of the shared reference electrode 217 are non-limiting. For example, the shared reference electrode 217 can be positioned along any of the empty spaces 243, at the location of the plurality of shorted reference nodes 219, along the interior capsule surface 123b of the capsule 112, along the first and the second widthwise segments 245 and 246, and/or any other position along the interior surface 205 of the arm-wearable device 210.

Figure 3:
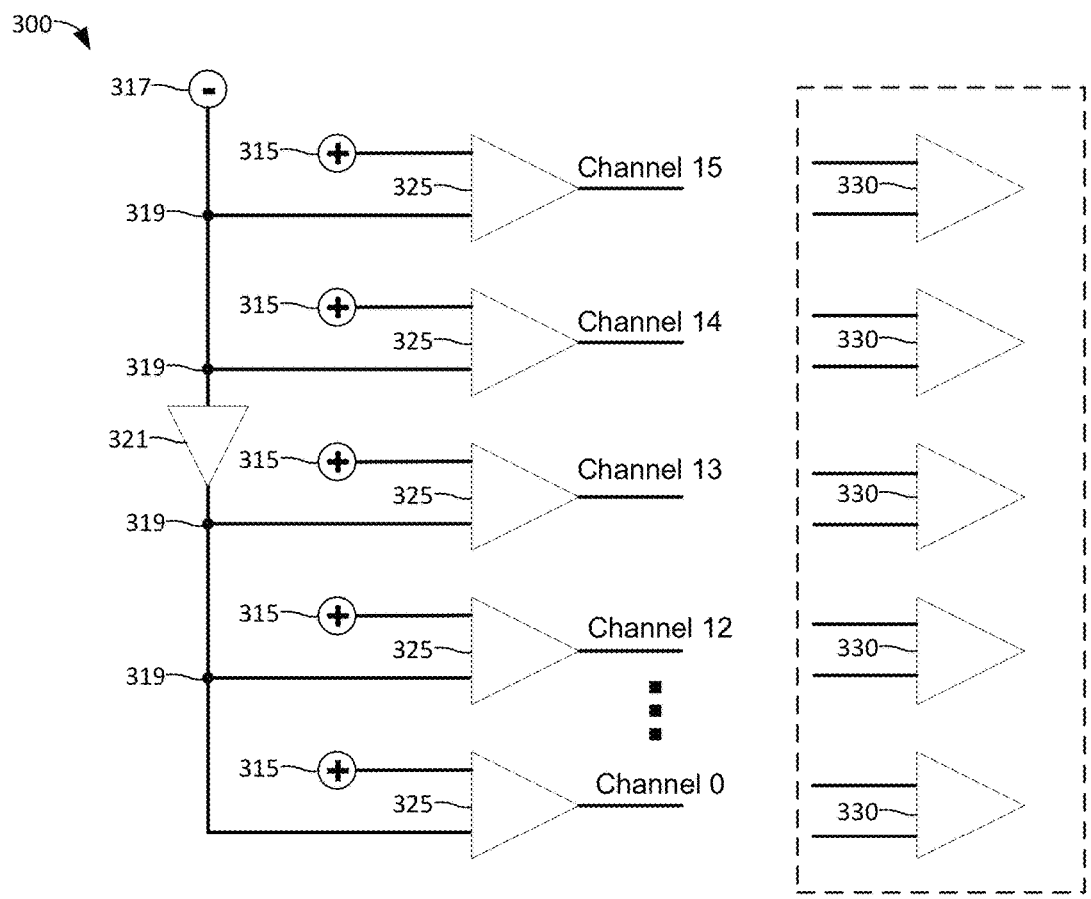
FIG. 3 illustrates a high-level schematic of an arm-wearable device, in accordance with some embodiments.
Figure 4:
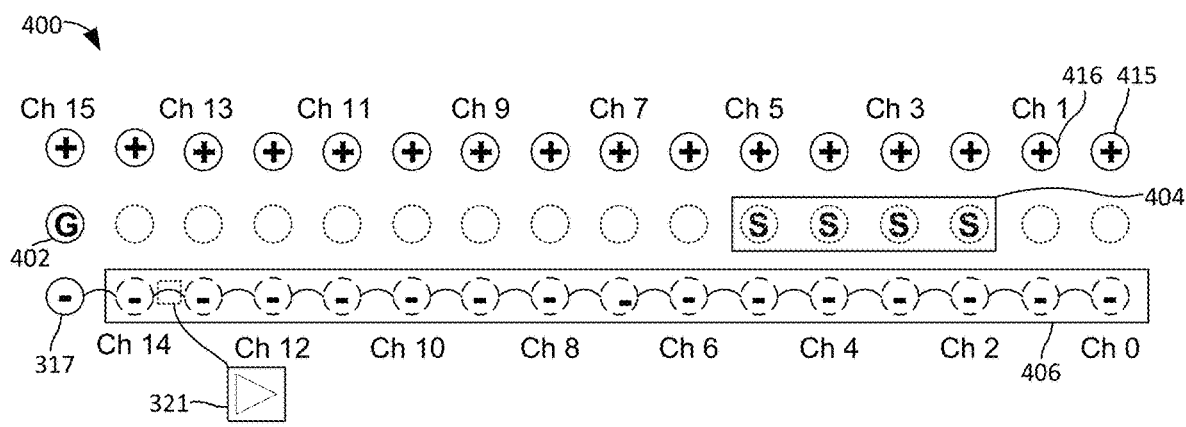
FIG. 4 illustrates another embodiment of an arm-wearable device, in accordance with some embodiments.

As described above, the reference neuromuscular signal is used in conjunction with the first electrode and second electrode 215 and 216 to form, in part, at least the first and second channels for detecting neuromuscular signals. The reference neuromuscular signal can be compared to respective neuromuscular signals detected by the first electrode and the second electrode 215 and 216 to allow for a determination of a motor action that a user intends to perform. In some embodiments, the reference neuromuscular signal is an unbuffered signal. Alternatively, as shown in FIGS. 3 and 4, in some embodiments, the reference neuromuscular signal is configured to be buffered before it is compared to the respective neuromuscular signals detected by the first electrode and the second electrode 215 and 216. The buffering of the reference neuromuscular signal is configured to reduce effects of noise and interference coupling into the shared reference electrode (e.g., power line interference or an unwanted factor, such as a stray effect of alternating current fields or other noise in bipotential recordings, that interferes with the analysis of neuromuscular signals, and this unwanted factor occur in a frequency range of 50-60 Hz) at the shared reference electrode 217.

In some embodiments, circuitry (e.g., one or more processors, such as CPU 1526 and/or MCU 1552 of wearable device 110; FIGS. 1A-1C and FIG. 15) is configured to compare respective neuromuscular signals detected by respective one or more electrodes of each of the at least fifteen channels to the reference neuromuscular signal to allow for the determination by one or more processors of the arm-wearable device of the motor action that the user intends to perform with their hand.

The first embodiment of the arm-wearable device 210 includes an additional electrode operating as a ground (e.g., ground electrode 230). The ground electrode 230 can be positioned without any adjacent electrodes. Alternatively, in some embodiments, the ground electrode 230 is laterally adjacent to the shared reference electrode 217 and aligned along the third widthwise segment 247 of the interior surface 205. In some embodiments, the ground is used for common mode rejection. One purpose of the ground is to prevent power line noise from interfering with the small biopotential signals (e.g., the neuromuscular signals discussed herein) of interest. In some embodiments, the ground electrode 230 is configured to bias the circuitry. Similar to the shared reference electrode 217, the first electrode 215, and the second electrode; the ground electrode 230 can be placed on any position along the interior surface 205 of the arm-wearable device 210.

In some embodiments, the first embodiment of the arm-wearable device 210 includes the one or more shield electrodes 240. In some embodiments, the arm-wearable device includes a single shield electrode 240. The one or more shield electrodes 240 are configured operate as a shield and reduce or eliminate power line interference. In some embodiments, each electrode of the one or more shield electrodes 240 is aligned along a respective widthwise segment of the interior surface 205 of the arm-wearable device 210. In some embodiment, the one or more shield electrodes 240 are laterally adjacent to respective one or more electrodes for sensing neuromuscular signals (e.g., the first electrode 215, the second electrode 216, the shared reference electrode 217, and/or the one or more electrodes aligned along a distinct widthwise segment of the wearable structure). In some embodiments, a first shield electrode of the one or more shield electrodes 240 is positioned adjacent to a second shield electrode of the one or more shield electrodes 240 (e.g., as shown by shield electrode in the third and fourth widthwise segments 248 and 249, which are adjacent to one another). In some embodiments, each electrode of the one or more shield electrodes 240 is separated a predetermined distance ("ds"; e.g., 10-20 mm). In some embodiments, the one or more shield electrodes 240 includes at least four shield electrodes. Alternatively, in some embodiments, at least one shield electrode of the one or more shield electrodes 240 is positioned such that there are no adjacent shield electrodes (e.g., as shown by shield electrode in the fourth and fifth widthwise segments 249 and 251, which are separated by at least one widthwise segment). In some embodiments, no shielding electrode 240 is used. Similar to the ground electrode 230, the shared reference electrode 217, the first electrode 215, and the second electrode; the one or more shield electrodes 240 can be placed on any position along the interior surface 205 of the arm-wearable device 210.

By using a shared reference electrode 217, the total number of channels can be increased (or left at a predetermined amount) while the total number of physical electrodes on an arm-wearable device is reduced, which improves the overall comfort for a user. Alternatively, more channels can be incorporated into an arm-wearable device without making the arm-wearable device bulky and uncomfortable to the user. More specifically, by having each electrode configured to sense neuromuscular signals form, in part, a channel with the shared reference electrode 217, the arm-wearable device can be designed with any number of channels without requiring pairs of physical electrodes to form a channel thereby reducing the total number of electrodes as well as the size of the arm-wearable device. User comfort is further improved as less electrodes need to make contact with (or depress into) the user's skin (e.g., because the widthwise segments discussed above can be configured to have just one neuromuscular-signal-sensing electrode rather than a pair, or more, of neuromuscular-signal-sensing electrodes) and reduces the overall weight of the arm-wearable device while still enabling the arm-wearable device to detect stable and reliable neuromuscular signal that can be used to determine a motor action that the user intends to perform with their hand. While electrode pairs are not required to from a channel, electrode pairs can be used in conjunction with the shared reference to further improve reliability and/or accuracy of the sensed neuromuscular signals.

In FIG. 2B, a second configuration of an arm-wearable device 250 is shown. The second configuration of the arm-wearable device 250 shows the first electrode 215 positioned along a first widthwise segment 255 of the interior surface 205 and the second electrode 216 positioned along a second widthwise segment 256 of the interior surface 205. As described above, each of the first and second electrodes 215 and 216 form respective channels (when used in conjunction with the shared reference electrode 217). As shown in the second embodiment of the arm-wearable device 250, the first electrode 215 (or any other electrode) can be positioned as part of the capsule 112 (e.g., interior capsule surface 123b; FIGS. 1A-1C). In the second embodiment of the arm-wearable device 250, the second configuration of an arm-wearable device 250 includes at least five channels for sensing neuromuscular signals, each of the at least five channels including an electrode aligned along a distinct portion of the wearable structure.

The second configuration of an arm-wearable device 250 also shows the shared reference electrode 217 aligned along a third widthwise segment 257, distinct from the first and the second widthwise segments 255 and 256, of the interior surface 205. In some embodiments, the third widthwise segment 257 is positioned as part of the capsule 112 (e.g., interior capsule surface 123b). In some embodiments, the ground electrode 230 and a shield electrode 240 are also aligned along the interior surface 205 as part of the capsule 112 (e.g., interior capsule surface 123b).

A third configuration of an arm-wearable device 270, as shown in FIG. 2C, illustrates one or more electrodes for sensing neuromuscular signals in a zigzagging pattern. For example, the first electrode 215 of the third configuration of the arm-wearable device 270 can be aligned along a first portion of the interior surface 205 and the second electrode 216 can be aligned along a second portion of the interior surface 205 at a predetermined angle (e.g., 15 degrees, 30 degrees, 45 degrees, etc.) relative to an edge 272 of the interior surface 205 (e.g., angle α). FIG. 2C further shows one or more electrodes 276 that can be removed from the arm-wearable device 270. More specifically, one or more electrodes 276 can be added or removed from the third configuration of the arm-wearable device 270 to adjust the number of channels included in the arm-wearable device 270 (e.g., channels formed using the shared reference electrode 217 as described above in reference to FIGS. 2A and 2B). For example, the third configuration of the arm-wearable device 270 can include at least 5 channels, at least 6 channels, at least seven channels, etc. Although not shown, the third configuration of the arm-wearable device 270 also includes the plurality of shorted reference nodes 219.

FIG. 2D shows a fourth configuration of an arm-wearable device 290. The fourth configuration of the arm-wearable device 290 has the shared reference electrode 217 and the first electrode 215 positioned along a first widthwise segment of the interior surface 205. Additional sensors 292 for sensing neuromuscular signals are positioned along distinct portions of the interior surface 205. As described above, the additional sensors 292, when used in conjunction with the shared reference electrode 217, form respective channels. In some embodiments, one or more of the additional sensors 292 are optional (as represented by a dotted outline of the electrodes). Although not shown, the fourth configuration of the arm-wearable device 290 also includes the plurality of shorted reference nodes 219.

The above examples are non-limiting. Different configurations and/or numbers of electrodes can be used. For example, in alternative embodiments, the widthwise segments might be wider such that the widthwise segment can include more than one electrode (e.g., first electrode 215), more than three electrodes, etc. Similarly, in another example, the widthwise segments might be narrower such that the widthwise segment can include no more than two electrodes or more than one electrode.

As described above, in reference to FIGS. 1A-1C, one or more processors (e.g., CPU 1526 and/or MCU 1552) of the first and second embodiment of the arm-wearable device 200 and 250 are configured to compare (i) the respective neuromuscular signals detected by the first electrode to the reference neuromuscular signal and (ii) the respective neuromuscular signals detected by the second electrode to the reference neuromuscular signal to allow for a determination by one or more processors of the arm-wearable device of a motor action that the user intends to perform with their hand. In some embodiments, the respective neuromuscular signals detected by the first electrode and the second electrode and the reference neuromuscular signal are detected along a same axis or distinct axes of the user's wrist. Further, as the skilled artisan would also appreciate, a system can also include third electrodes fourth electrodes, etc., each of which can be aligned along respective portions of the of the interior surface 205 of the arm-wearable device and have sensed neuromuscular signals compared to the reference neuromuscular signals detected by the shared reference electrode, as is explained in more detail below.

FIG. 3 illustrates a high-level schematic of an arm-wearable device, in accordance with some embodiments. The high-level schematic 300 includes one or more electrodes 315, a shared reference electrode 317, a plurality of shorted reference nodes 319, a first buffer 321, and a plurality of distinct buffers 325. In some embodiments, the plurality of distinct buffers 325 are instrumentation or differential amplifiers. As shown in the high-level schematic 300, in some embodiments, one or more optional buffers 330 are coupled to the respective outputs of the plurality of distinct buffers 325. The one or more optional buffers 330, in some embodiments, include differential amplifiers and/or instrumentation amplifiers. In some embodiments, instrumentation amplifier are used to measure neuromuscular signals in the presence of a noise. In some embodiments, the differential amplifier are used to mitigate noise in the neuromuscular signals. The one or more electrodes 315, the shared reference electrode 317, and the plurality of shorted reference nodes 319 are analogous to the one or more first and second electrodes 215 (e.g., any of the electrodes 315 can be examples of the first or second electrodes, as well as third, fourth, or fifth electrodes, for different respective sensing channels as shown in FIG. 3), the shared reference electrode 217, and the plurality of shorted reference nodes 219, respectively, described above in reference to FIGS. 2A-2D.

Each buffer of the plurality of distinct buffers 325 is associated with a respective channel of an arm-wearable device (e.g., the different embodiments of an arm-wearable device described above in reference to FIGS. 2A-2D). A detected neuromuscular signal from each electrode of the one or more electrodes 315 and a reference neuromuscular signal of each shorted reference node of the plurality of shorted reference nodes 319 are provided to a respective buffer of the plurality of distinct buffers 325. For example, a first distinct buffer of the plurality of distinct buffers 325 associated with channel 15 is configured to receive a detected neuromuscular signal from a first electrode of the one or more electrodes 315 and the reference neuromuscular signal of a first shorted reference node of the plurality of shorted reference nodes 319. In another example, a second buffer of the plurality of distinct buffers 325 associated with channel 14 is configured to receive a detected neuromuscular signal from a second electrode of the one or more electrodes 315 and the reference neuromuscular signal of a second shorted reference node of the plurality of shorted reference nodes 319. In some embodiments, the circuitry (e.g., a CPU 1526 and/or MCU 1552; FIG. 15) that is configured to compare the respective neuromuscular signals detected by the one or more electrodes to the reference neuromuscular signal includes an instrumentation amplifier or a differential amplifier.

In some embodiments, the first buffer 321 is coupled between shorted reference nodes of the plurality of shorted reference nodes 319 configured to provide the reference neuromuscular signal to channels 14 and 13. Use of the first buffer 321 reduces (e.g., by 65%-95%) or eliminates the effects of noise and interference coupling into the shared reference electrode. In some embodiments, the first buffer 312 reduces or eliminates power line interference in the reference neuromuscular signal and balances the impedance in the arm-wearable device.

In some embodiments, each channel is further coupled to a respective buffer of the one or more optional buffers 330. Similar to the first buffer 321, the one or more optional amplifiers 330 are configured to reduce or eliminate the effects of noise and interference coupling into the shared reference electrode. In some embodiments, the one or more optional amplifiers 330 are configured to reduce or eliminate the power line interference in the reference neuromuscular signal and balances the impedance in the arm-wearable device.

FIG. 4 illustrates another embodiment of an arm-wearable device, in accordance with some embodiments. As shown in FIG. 4, a first electrode 415 and a second electrode 416 (which form and are part of channels 0-15), a shared reference electrode 417, a first buffer 321, a ground electrode 402, and a plurality of shorted reference nodes 406. In some embodiments, the arm-wearable device includes one or more shield electrodes 404. The first electrode 415, the second electrode 416, and the shared reference electrode 417 are similar to the first electrode 215, the second electrode 216, and the shared reference electrode 217 (described above in reference to FIGS. 2A-2D), respectively. The ground electrode 402, one or more shield electrodes 404, and the plurality of shorted reference nodes 406 are analogous to the ground electrode 230, the one or more shield electrodes 240, and the plurality of shorted reference nodes 219 (described above in reference to FIGS. 2A-2D), respectively. In some embodiments, the first buffer 321 is positioned between adjacent channels (e.g., channels 13 and 14) of the respective channels and configured to mitigate interference at the shared reference electrode (e.g., reduce or eliminate power line interference)

Electrodes in dotted lines in FIG. 4 represent electrodes that have been removed from the arm-wearable device. In the embodiment of the arm-wearable device shown in example view 400, the shared reference node 417 is aligned along a third portion of an interior surface of an arm-wearable device (as described above in reference to FIGS. 2A-2D). The embodiment of the arm-wearable device shown in FIG. 4 is configured to perform one or more features of the arm-wearable devices described above in reference to FIGS. 1A-3.

Figure 5A:
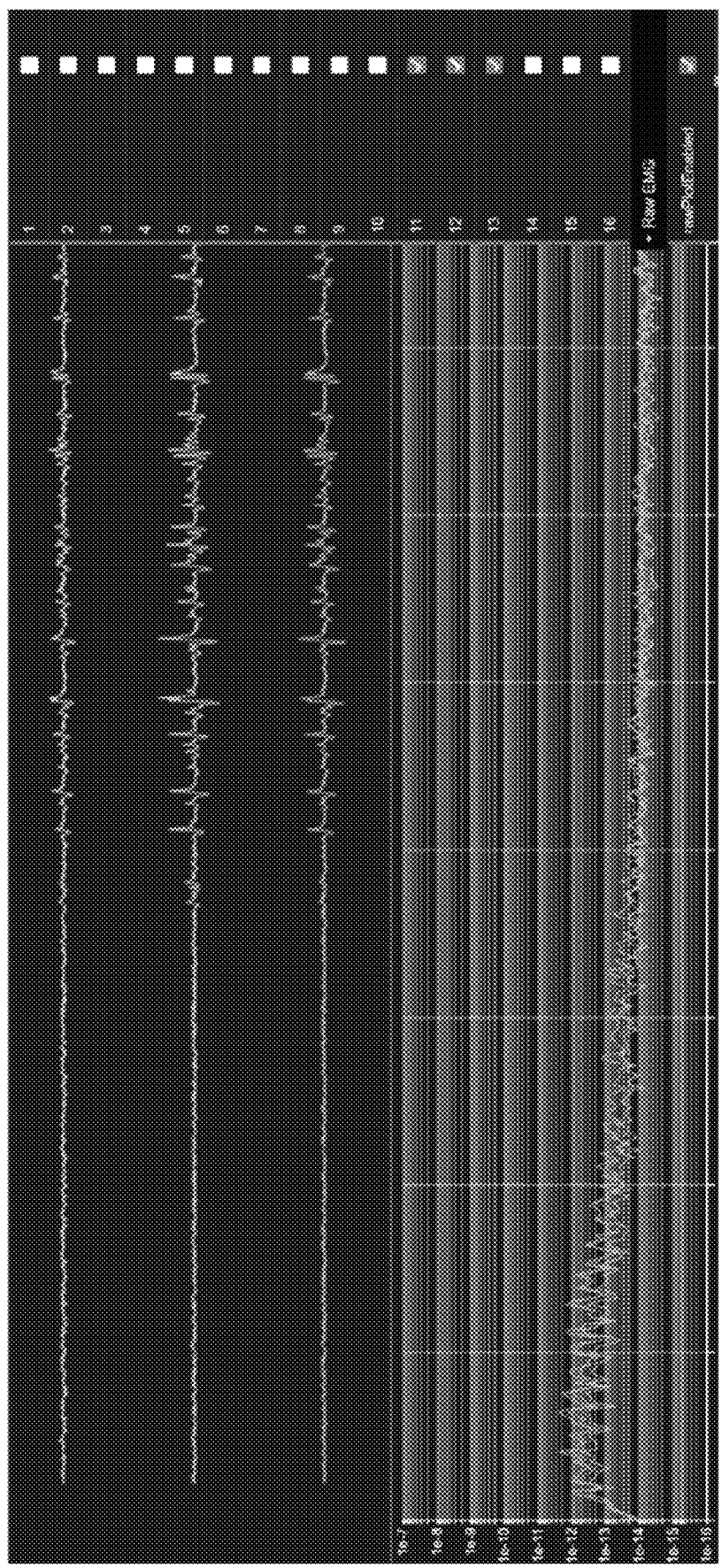
FIGS. 5A and 5B illustrate movements by one or more digits detected by an arm-wearable device, in accordance with some embodiments.
Figure 5B:
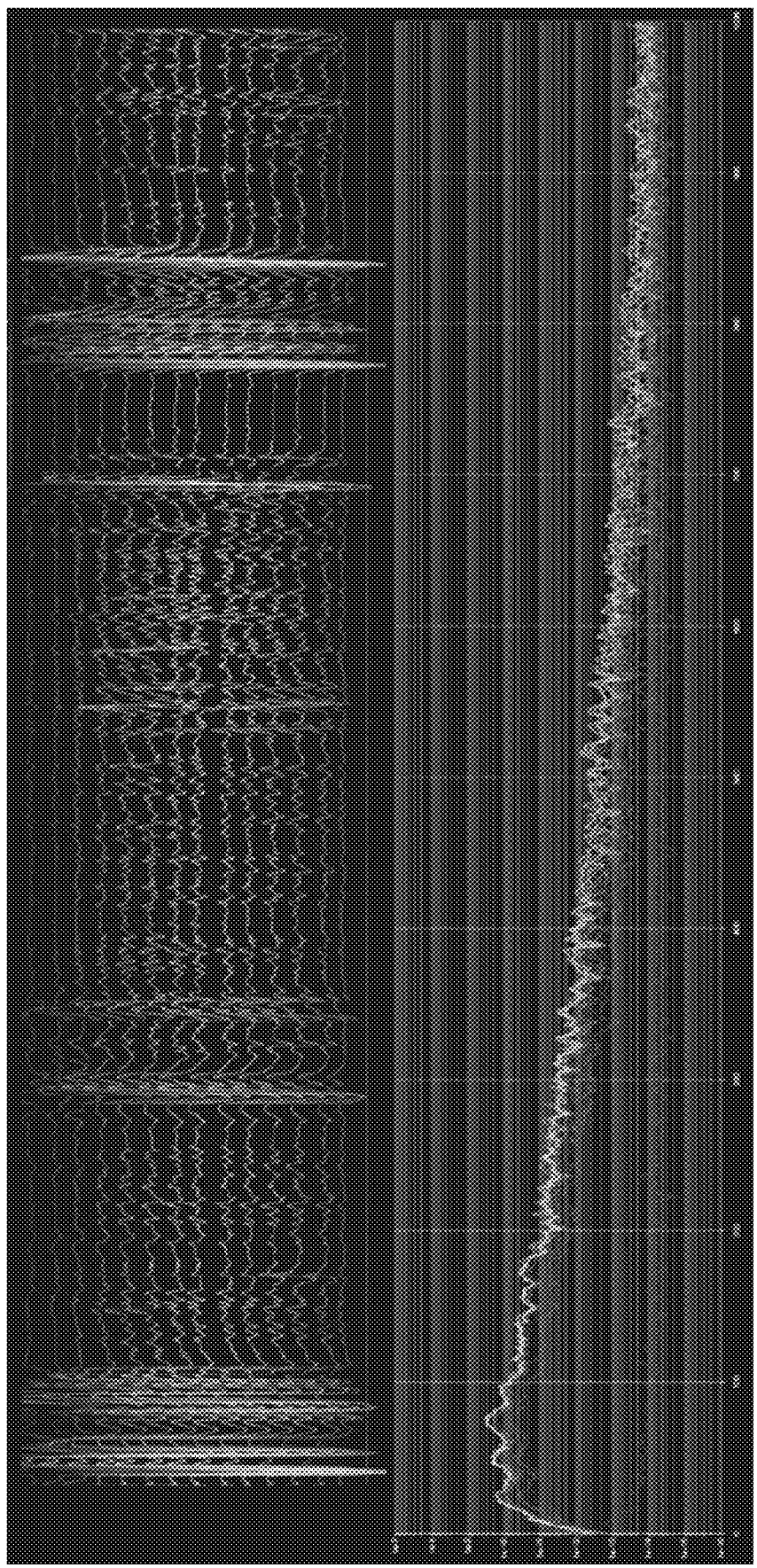

FIGS. 5A and 5B illustrate neuromuscular signals detected in conjunction with movements by one or more digits detected by an arm-wearable device, in accordance with some embodiments. More specifically, FIGS. 5A and 5B show visual representations of spikes (i.e., detected neuromuscular signals) detected by the arm-wearable device using a shared reference electrode in accordance with FIGS. 2A-4. FIGS. 5A and 5B are provided as sample readings. FIG. 5A represents neuromuscular signals detected with three active channels (e.g., channels 11-13). FIG. 5B represents neuromuscular signals detected with all channels active (e.g., 16 channels; 15 channels active for sensing neuromuscular signals and one channel for sensing a reference neuromuscular signal via the shared reference node).

Figure 6:
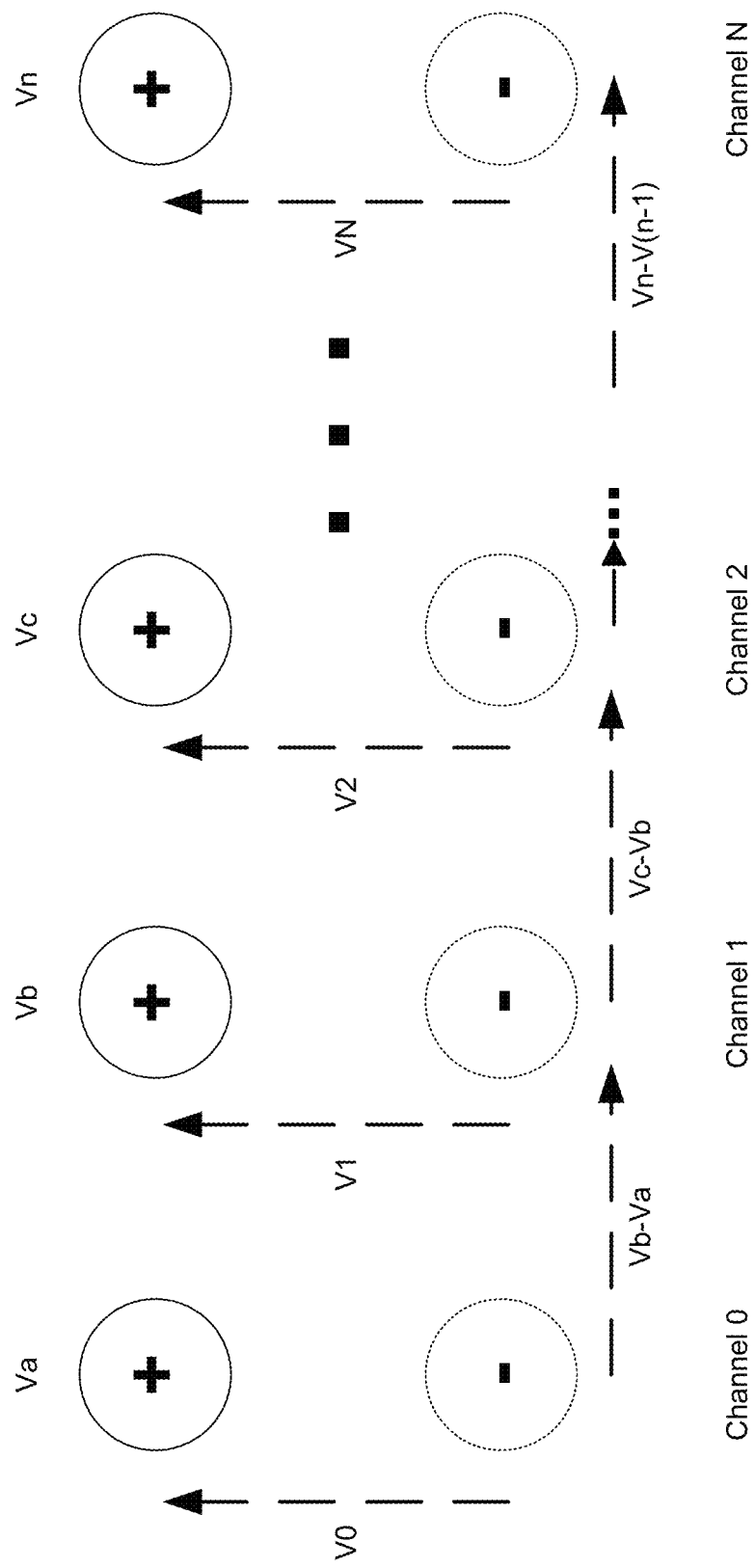
FIG. 6 illustrates an embodiment of an arm-wearable device determining motor actions to be performed based on neuromuscular signal differentials sensed along at least two different directions, in accordance with some embodiments.

FIG. 6 illustrates an embodiment of an arm-wearable device for determining motor actions to be performed based on neuromuscular signal differentials sensed along at least two different directions, in accordance with some embodiments. The arm-wearable device can be any arm-wearable device described above in reference to FIGS. 1A-4 and below in reference to FIGS. 14A-15. For example, the arm-wearable device can include a predetermined number of channels; each channel formed by a shared reference electrode (e.g., shared reference electrode 217; FIGS. 2A-2D) used in conjunction with a respective electrode (e.g., a first electrode 215; FIGS. 2A-2D) configured to detect neuromuscular signals (e.g., in FIG. 6, one or more negative (−) electrodes (shown with a dotted outline) are similar to the plurality of shorted reference nodes 219; FIGS. 2A-2D). Alternatively, in some embodiments, the arm-wearable device includes a predetermined number of channels each formed by two or more electrodes aligned along a respective distinct widthwise segment of the interior surface and configured to detect neuromuscular signals. In some embodiments, the channels are dynamically defined (e.g., the arm-wearable device can define a channel to include at least four electrodes, at least two electrodes, and/or channels of varying channel sizes (e.g., a first channel can be two electrodes and a second channel is four electrodes)). A portion of each electrode contacts the user's skin above respective neuromuscular pathways of the user when the wearable structure is worn by the user. For ease of discussion, FIG. 6 shows pairs of physical electrode aligned along distinct widthwise segments of an interior surface; however, as the skilled artisan would appreciate (and as noted above), channels formed using one or more electrodes in conjunction with a shared reference electrode (and aligned along different portions of an interior surface) can be used to sense neuromuscular signal differentials along at least two different directions (i.e., the one or more negative (−) electrodes do not have to be physical electrodes).

In some embodiments, the arm-wearable device, via one or more processors (e.g., CPU 1526, MCU 1552, etc.; FIG. 15), determines a first plurality of signal differentials between respective neuromuscular signal values sensed by respective two or more of electrodes of each respective channel of the predetermined number of channels (this is referred to as an intra-channel signal differential). For example, for channel 0, a signal differential of the first plurality of signal differentials is the difference between the neuromuscular signals detected by the positive (+) and negative (−) electrodes in channel 0. In another example, for channel 1, a signal differential of the first plurality of signal differentials is the difference between the neuromuscular signals detected by the positive (+) and negative (−) electrodes in channel 1. Each signal differential of the first plurality of signal differentials provides intra-channel information concerning neuromuscular activity in a widthwise direction of the interior surface of the wearable structure. Comparisons can also be made between the signals sensed between different channels and these are referred to as a second plurality of signal differentials, which reflect inter-channel signal differentials (comparing signals at channel 0 to those at channel 1, channel 2, and/or channel 3, etc.). The intra-channel signal differentials provide information about neuromuscular signals sensed in a first direction (widthwise direction), while the inter-channel signal differentials provide information about neuromuscular signals sensed in a second direction that is different from the first direction (lengthwise or radial direction). In some embodiments, each signal differential of the first and second pluralities of signal differentials is a voltage differential.

In some embodiments, the arm-wearable device, via the one or more processors, determines, for each channel of the predetermined number of channels, a signal average based on the respective neuromuscular signal values sensed by respective two or more electrodes of a respective channel of the predetermined number of channels. For example, for channel 0, the neuromuscular signals detected by the positive (+) and negative (−) electrodes in channel 0 are averaged to determine a first signal average. In another example, for channel 1, the neuromuscular signals detected by the positive (+) and negative (−) electrodes in channel 1 are averaged to determine a second signal average.

In some embodiments, the arm-wearable device, via the one or more processors, determines a second plurality of signal differentials by comparing respective signal averages between different channels of the predetermined number of channels. In some embodiments, each signal differential of the second plurality of signal differentials is the difference between respective signal averages of at least two adjacent channels (e.g., channels 0 and 1 are adjacent channels because they are located next to one another, but comparisons between channels that are further apart, such as between channels 0 and 2 or 0 and N are also within the scope of this disclosure as the skilled artisan will appreciate upon reading these descriptions) of the predetermined number of channels. For example, a signal differential of the second plurality of signal differentials is determined based on a signal difference between the first signal average determined based on the neuromuscular signals detected by the positive (+) and negative (−) electrodes in channel 0 and the second signal average determined based on the neuromuscular signals detected by the positive (+) and negative (−) electrodes in channel 1. In some embodiments, each signal average based on respective neuromuscular signal values sensed by respective two or more electrodes of a respective channel of the predetermined number of channels is an average voltage measured with respect to ground. Each signal differential of the second plurality of signal differentials provides inter-channel information concerning neuromuscular activity in a radial direction around the user's wrist that is substantially perpendicular to the widthwise direction.

In some embodiments, the arm-wearable device, via the one or more processors, determines signal noise between the first plurality of signal differentials and the second plurality of signal differentials, which can be used by the arm-wearable device to provide (i.e., generate) a mitigating signal to reduce the signal noise. In some embodiments, the arm-wearable device uses passive noise-mitigating techniques (e.g., hardware-enabled filters, resistors, and/or other non-active components). Alternatively, or additionally, in some embodiments, the arm-wearable device uses passive noise-mitigating techniques (e.g., generating an additional signal to cancel or reduce the determined signal noise, or active hardware components, such as op amps, instrumentation amplifiers, etc.). In some embodiments, the arm-wearable device drives an anti-phase signal to the user's wrist to reduce signal noise.

As described above, the arm-wearable device determines a motor action that the user intends to perform with their hand based on the data about the neuromuscular signals. For purposes of this disclosure, in some embodiments, the data about the neuromuscular signals includes the intra-channel information concerning neuromuscular activity in a widthwise direction of the interior surface of the wearable structure and/or inter-channel information concerning neuromuscular activity in a radial direction around the user's wrist that is substantially perpendicular to the widthwise direction. The above-disclosed methods and systems for determining the signal differentials are used to generate additional information in determining a motor action. More specifically, the disclosed method and systems generate intra-channel information and/or inter-channel information without the use of additional electrodes. The additional information improves the accuracy and detection of a motor action that the user intends to perform with their hand based on the data about the neuromuscular signals.

Although the above examples describe signal differentials based on voltage, one or more other signal characteristics can be used to determine the intra-channel information concerning neuromuscular activity in a widthwise direction of the interior surface of the wearable structure and interchannel information concerning neuromuscular activity in a radial direction around the user's wrist that is substantially perpendicular to the widthwise direction. For example, in some embodiments, signal frequency and/or phase detected by the electrodes forming the predetermined number of channels can also be used to determine the intra-channel information and the inter-channel information.

Figure 7:
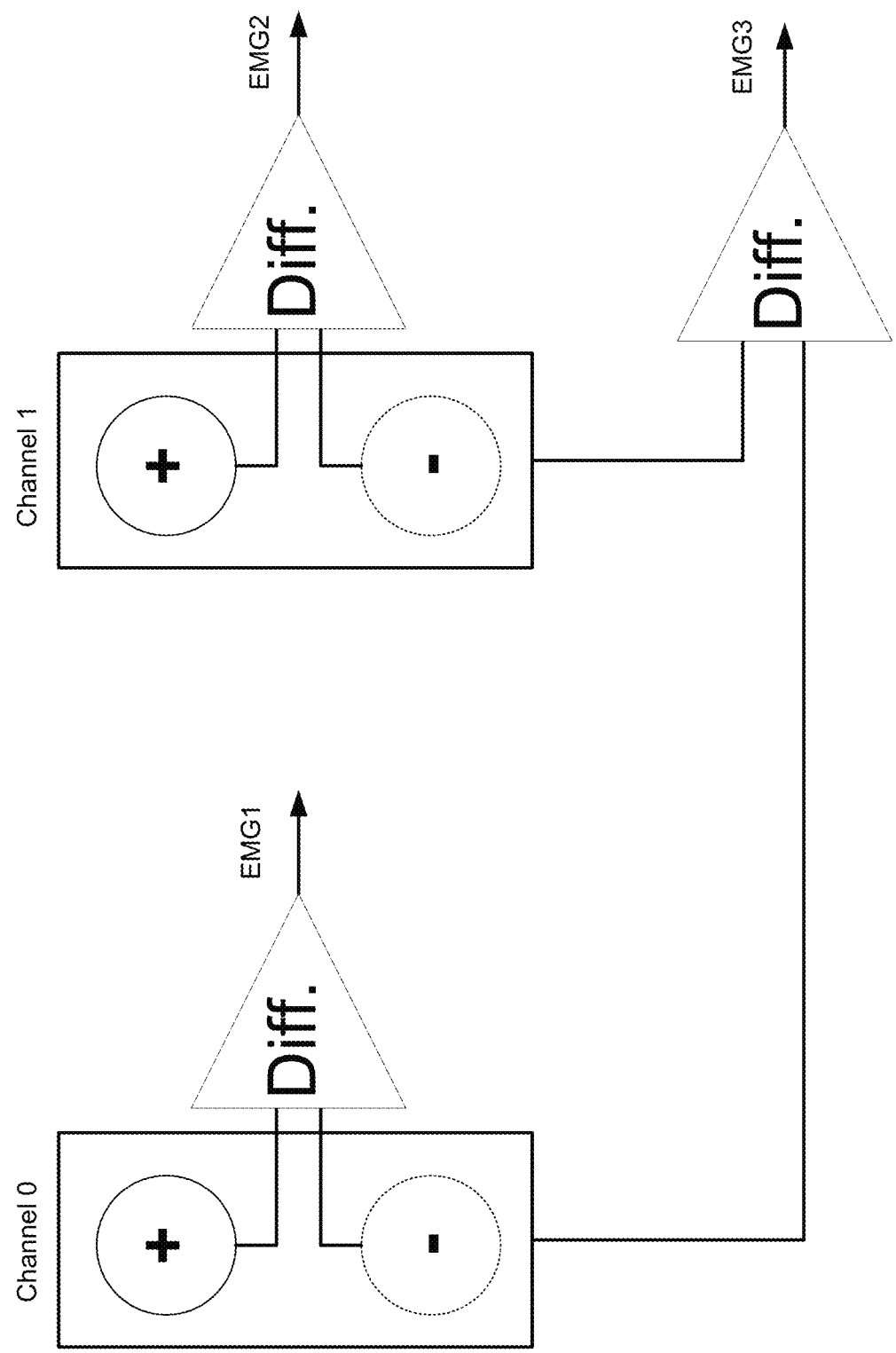
FIG. 7 is a high-level block diagram of an arm-wearable device for sensing neuromuscular signals along a radial direction (e.g., a lengthwise direction that is substantially perpendicular to a widthwise direction, which is referred to as radial since the lengthwise direction wraps around the user's arm radially when the device is worn or donned by a user) using one or more channels, in accordance with some embodiments.

FIG. 7 is a high-level block diagram of an arm-wearable device for sensing neuromuscular signals in a radial direction using one or more channels, in accordance with some embodiments. In particular, high-level block diagram 700 shows two channels generating respective data about the neuromuscular signals (e.g., EMG 1 by channel 0 and EMG 2 by channel 1), as well as additional data about the neuromuscular signals based on the two channels. More specifically, as described above in reference to FIG. 6, the positive (+) and negative (−) electrodes of each channel are used to determine a first plurality of signal differentials, and a signal average of at least two channels is used to determine a second plurality of signal differentials. Additional information on the determination of the first and second plurality of signal differentials is provided above in reference to FIG. 6.

Figure 8A:
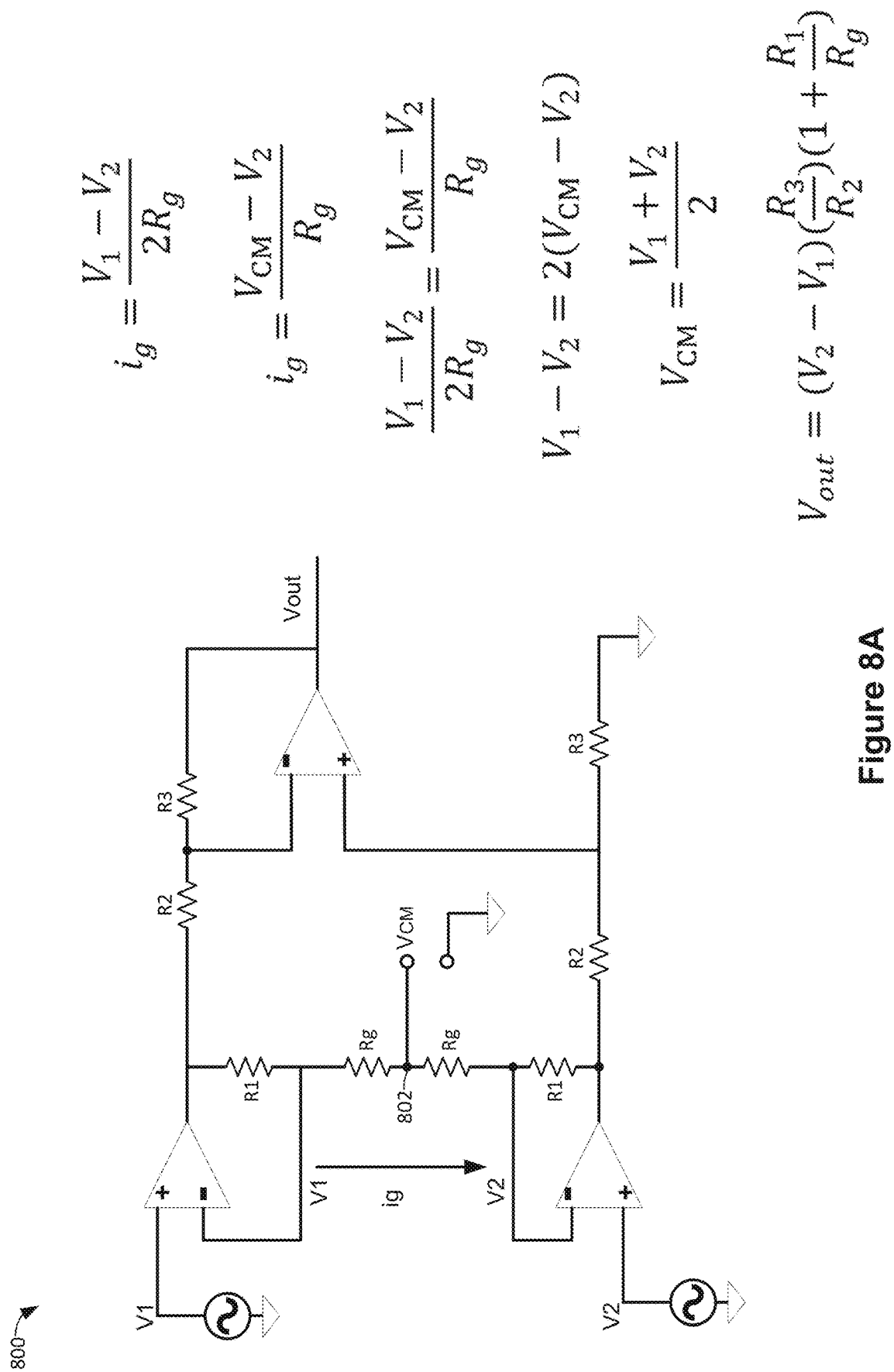
FIG. 8A illustrates a derivation of the common mode voltage equation with respect to circuit common of an arm-wearable device, in accordance with some embodiments.

FIG. 8A illustrates a derivation of the common mode voltage equation with respect to circuit common of an arm-wearable device, in accordance with some embodiments. Schematic 800 shows a circuit diagram of a system for detecting neuromuscular signals. In some embodiments, a common node 802 is used to sense neuromuscular signals along a radial direction. The common mode voltage ($V_{CM}$) is derived from the current ($i_g$) within the system, in accordance with some embodiments. As one non-limiting example, the current in the system can be defined as:

$$i_g = \frac{V_1 - V_2}{2R_g} \text{ and } i_g = \frac{V_{CM} - V_2}{g}$$

The two equations in this example can be used to solve for the common mode voltage, which is:

$$V_{CM} = \frac{V_1 + V_2}{2}$$

As shown by the derivation, the common mode voltage can be defined by the average of the two input voltages (with respect to circuit common, e.g., $V_1$ and $V_2$). The output voltage (V ow) is a function of the difference between $V_1$ and $V_2$ and can be defined as:

$$V_{out} = (V_2 - V_1)\left(\frac{R_3}{R_2}\right)\left(1 + \frac{R_1}{R_g}\right)$$

Figure 8B:
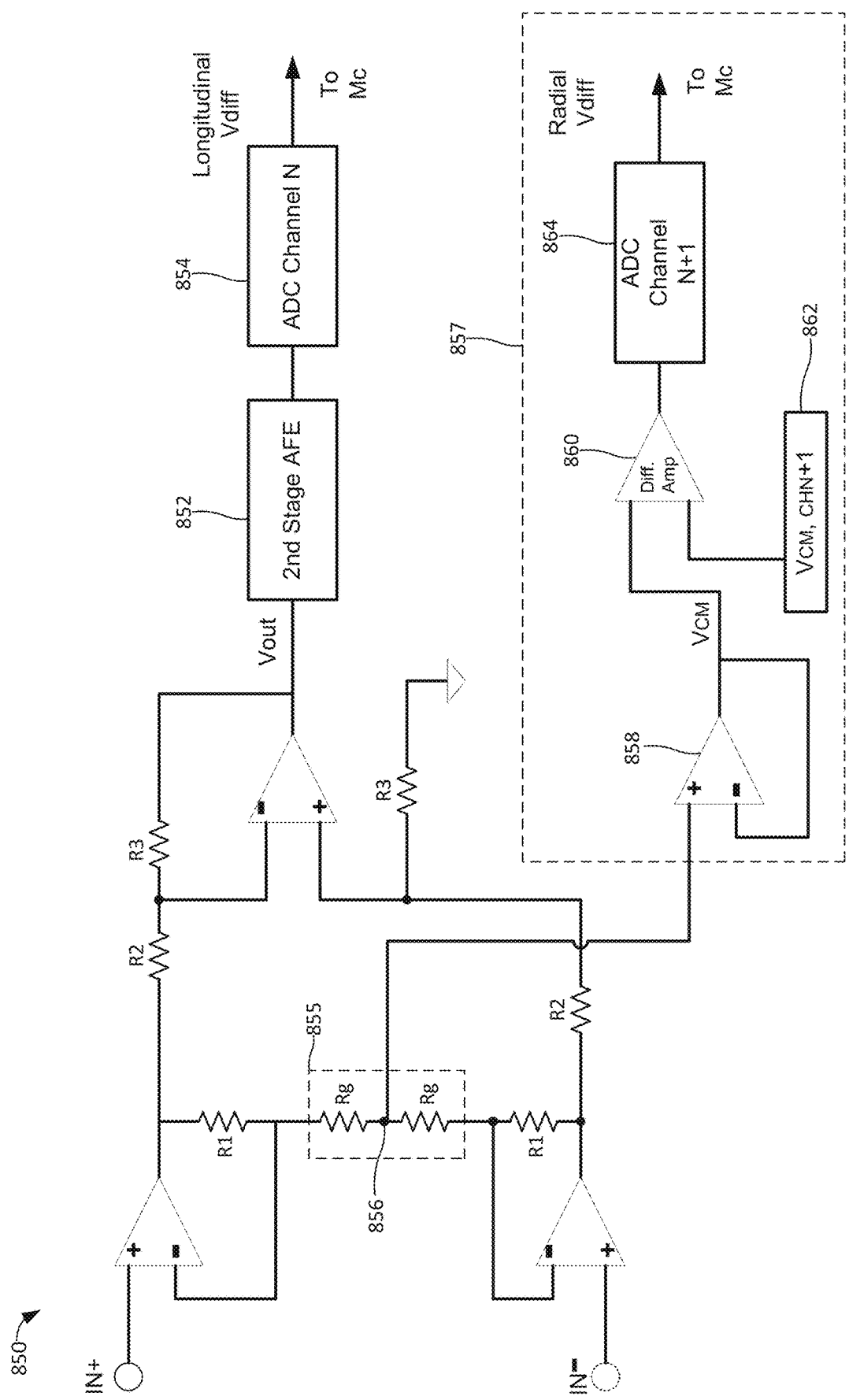
FIG. 8B is a detailed schematic of an arm-wearable device for sensing neuromuscular signals along a radial direction using one or more channels, in accordance with some embodiments.

As shown in FIG. 8B, the derived equations can be used to sense both longitudinal (neuromuscular activity in a widthwise direction of the interior surface) and radial data. In some embodiments, the reference point can be changed to something other than AGND; however, the differential measurement would be different.

FIG. 8B is a detailed schematic of an arm-wearable device for sensing neuromuscular signals in a radial direction using one or more channels, in accordance with some embodiments. Schematic 850 shows a circuit diagram of a channel an arm-wearable device. IN+ represents neuromuscular signals detected by a positive electrode and IN− represents neuromuscular signals detected by a negative electrode. IN+ and IN− are provided to a second stage analog front-end (AFE) 852. The output of the second stage AFE 852 is provided to an ADC channel 854 and sampled (e.g., at 2 khz) to generate longitudinal data (neuromuscular activity in a widthwise direction of the interior surface). As further shown in schematic 850, a connecting node 856 (between two identical gain resistors (Rg)) receives inputs from IN+ and IN−. The connecting node 856 (between the two identical gain resistors) is part of a first set of components 855 added to the arm-wearable device for sensing radial data (i.e., inter-channel information concerning neuromuscular activity in a radial direction).

The connecting node 856 is electrically coupled to an amplifier o buffer 858 as to not change the differential signal. The output of the buffer 858 is provided to a differential amplifier 860. The differential amplifier 860 receives an additional signal from a connecting node of an adjacent channel 862 (i.e., an adjacent channel that includes a similar structure as shown in schematic 850). The output of the differential amplifier 860 is provide to another ADC channel 854 and sampled (e.g., at 2 khz) to generate radial data. The buffer 858, the differential amplifier 860 and the other ADC channel 864 are part of a second set of components 857 added to the arm-wearable device for sensing radial data. The buffer 858 is added to sense or amplify a common mode signal (e.g., a voltage received from connecting node 856). In some embodiments, one differential amplifier (e.g., differential amplifier 860) is added for every two longitudinally differential channels (i.e., two adjacent channels (e.g., two adjacent longitudinal differentials shown in schematic 850)). Similarly, in some embodiments, one ADC (e.g., other ADC 864) is added for every two longitudinally differential channels (i.e., longitudinal differential shown in schematic 850). Although the above examples describe the use of adjacent channels, in some embodiments, any channels formed on an arm-wearable device can be used to determine inter-channel information concerning neuromuscular activity in a radial direction.

Figure 9A:
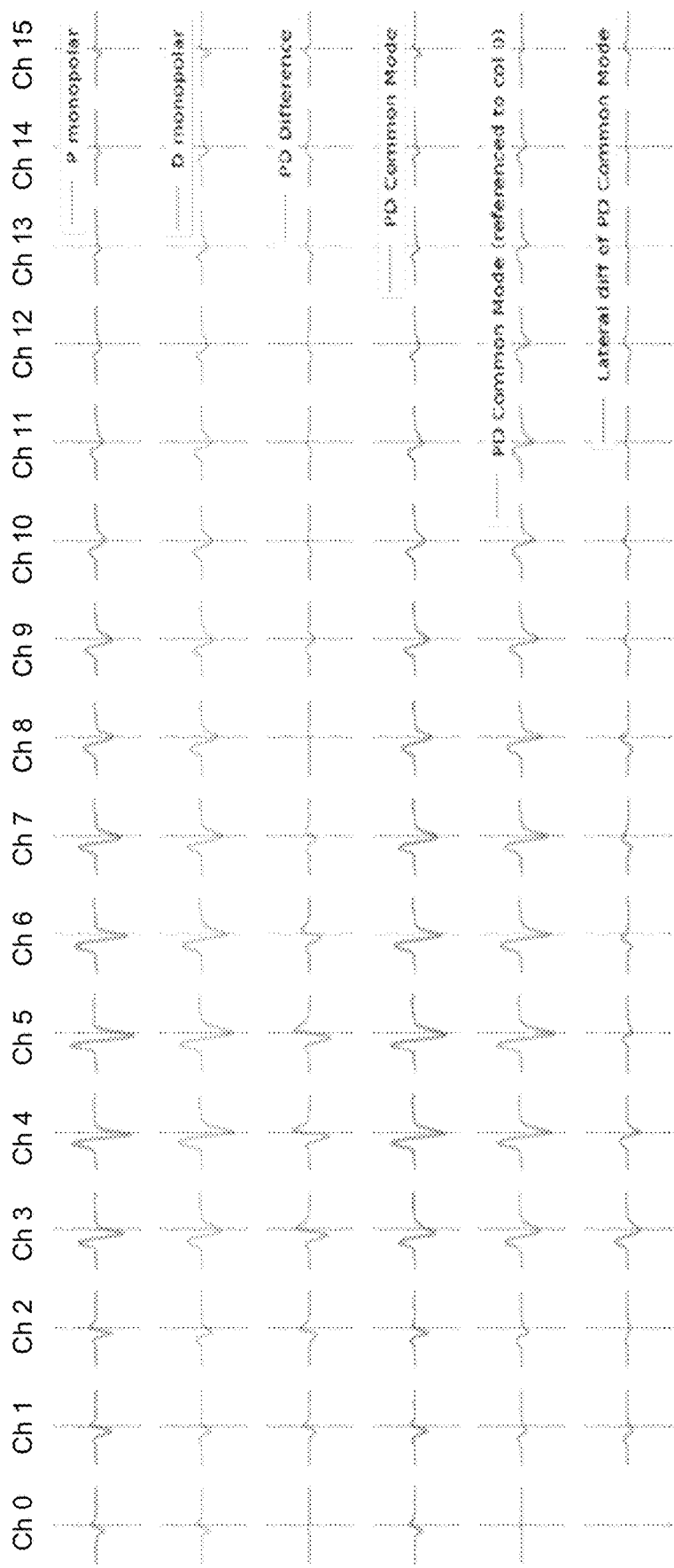
FIGS. 9A-9C are plots illustrating different readings at a sixteen-channel arm-wearable device, in accordance with some embodiments.
Figure 9B:
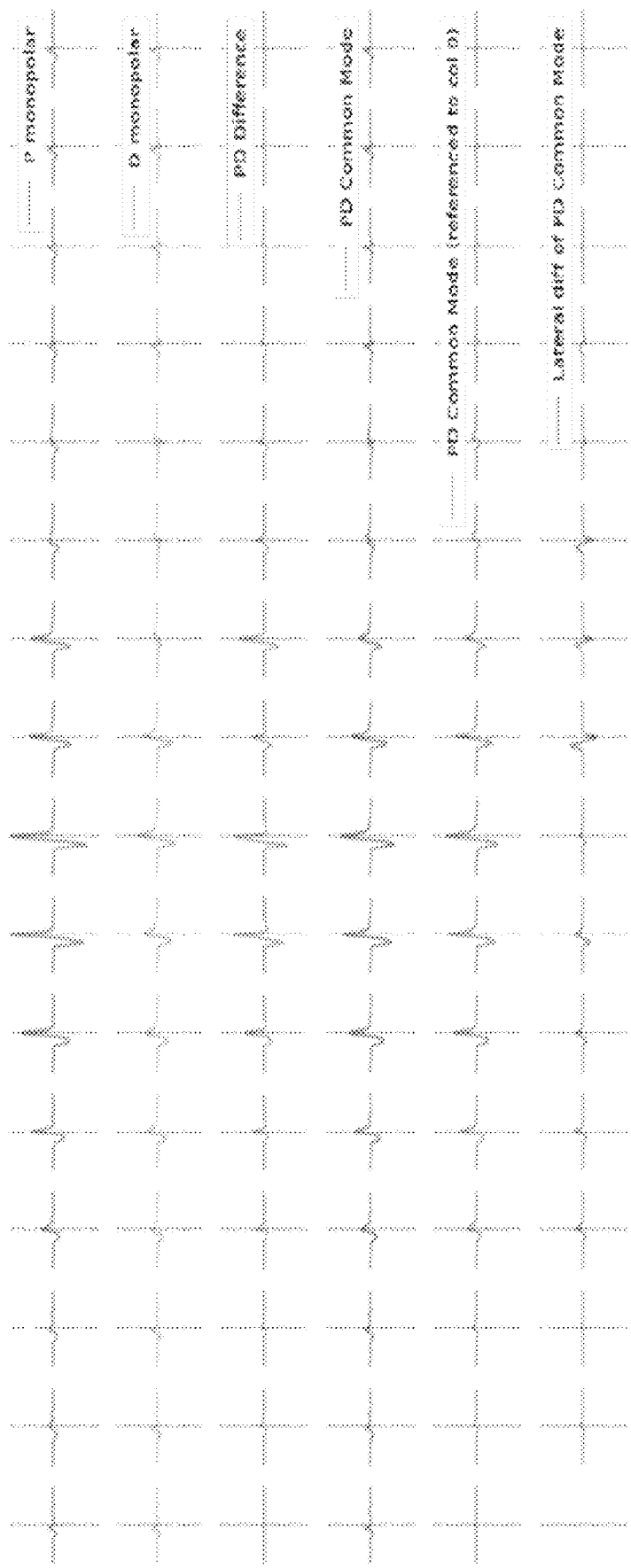
Figure 9C:
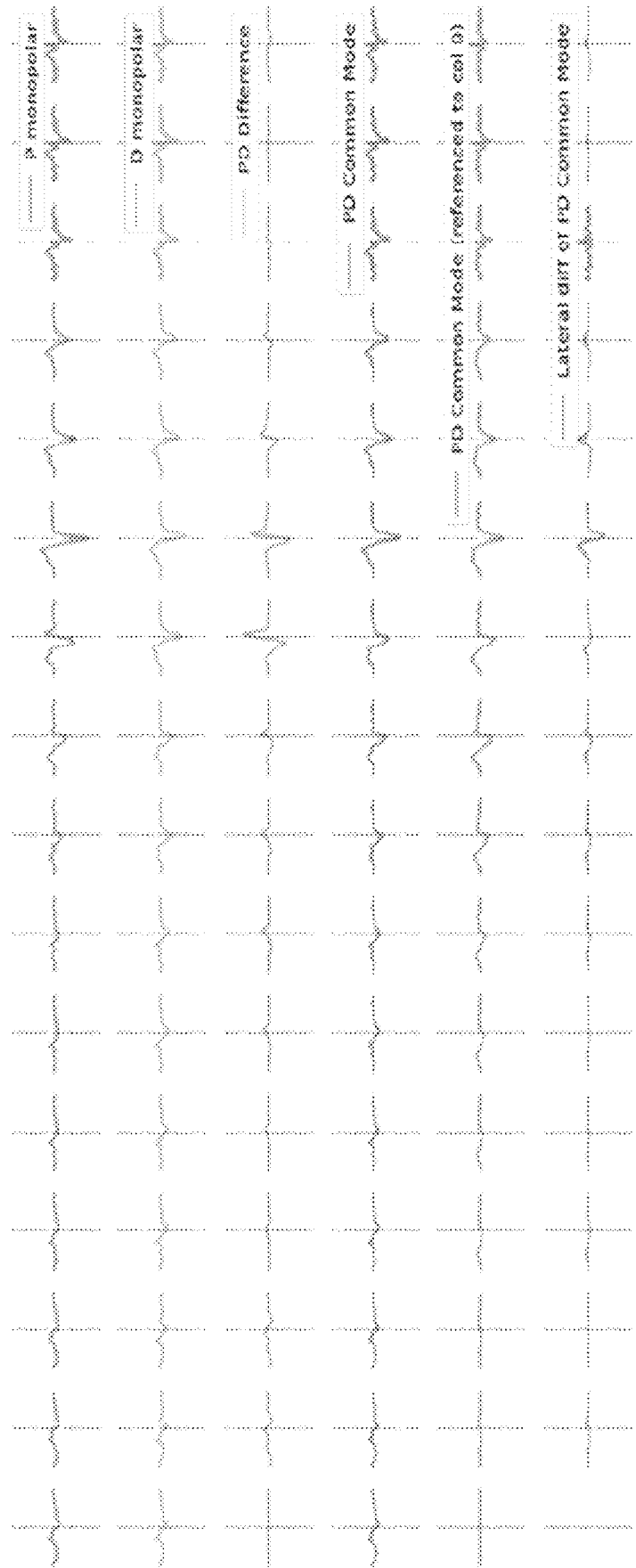

FIGS. 9A-9C are plots illustrating different readings at a sixteen-channel arm-wearable device, in accordance with some embodiments. Each illustrated channel is a per-channel triggered average of a plurality of spikes (e.g., approximately 100) from the arm-wearable device. FIG. 9A shows the readings of a first thumb curl, FIG. 9B shows the readings of a second thumb curl, and FIG. 9C shows the readings of an index pinky lift. The plots shown in FIGS. 9A-9C are captured without the use of a shared electrode node described above and as such includes a sixteen channel configuration. The green trace is meant to approximate what a motor unit action potential (MUAP) template would look like if it had been recorded by existing solutions. In the disclosed solution both the green trace (proximal-distal differential pair voltage difference, PD diff) and the purple common mode signal with respect to a ground reference at column 0 are available for determining a motor action. Although these emulated traces are looking at the effect on spike shape, there may be additional/other value when looking at the aggregate EMG, which may contain more distant (less superficial) sources.

FIG. 10 shows a detailed flow diagram of a method 1000 for sensing neuromuscular signals using a shared reference electrode of an arm-wearable device, according to some embodiments. Method 1000 can be performed at any arm-wearable device described above in reference to FIGS. 1A-4 and 6-8B. Operations (e.g., steps) of the method 1000 can be performed by one or more processors (e.g., CPU 1526, MCU 1552, etc.; FIG. 15) of an arm-wearable device. In some embodiments, the arm-wearable device is coupled with one or more sensors (e.g., various sensors shown in FIG. 15, such as a heart rate sensor 1558, EMG sensor 1546, SpO2 sensor 1554, altimeter 1548, thermal sensor or thermal couple, ambient light sensor, ambient noise sensor), a display 1513, a speaker 1574, an image sensor 1570, and a microphone 1572 to perform the one or more operations of FIG. 10. At least some of the operations shown in FIG. 10 correspond to instructions stored in a computer memory or computer-readable storage medium (e.g., storage 1502, ram 1503, and/or memory 1550; FIG. 15). Operations 1002-1016 can also be performed in part using one or more processors and/or using instructions stored in memory or computer-readable medium of an electronic device communicatively coupled to the arm-wearable device (e.g., a smartphone can perform operations 1002-1016 alone or in conjunction with the one or more processors of the arm-wearable device).

The method 1000 includes contacting (1002) a user's skin with the interior surface when the arm-wearable device is donned by the user. The arm-wearable device includes a first electrode, a second electrode, and a shared reference electrode. Examples of the first electrode, the second electrode, and the shared reference electrode are provided above in reference to FIGS. 2A-2D (e.g., the first electrode 215, the second electrode 216, and the shared reference electrode 217, respectively). A portion of each electrode of the first electrode, the second electrode, and the shared reference electrode contacts (1004) the user's skin above respective neuromuscular pathways of the user when the wearable structure is worn by the user. In some embodiments, the neuromuscular pathways are (1005) associated with muscles used for moving each of the user's digits, the user's wrist, and the user's forearm.

The method 1000 includes detecting (1006), via the first electrode and the second electrode, neuromuscular signals from the respective neuromuscular pathways of the user. The method 1000 also includes detecting (1008), via the shared reference electrode, a reference neuromuscular signal from neuromuscular pathways of the user that is compared to respective neuromuscular signals detected by the first electrode and the second electrode.

Figure 11B:
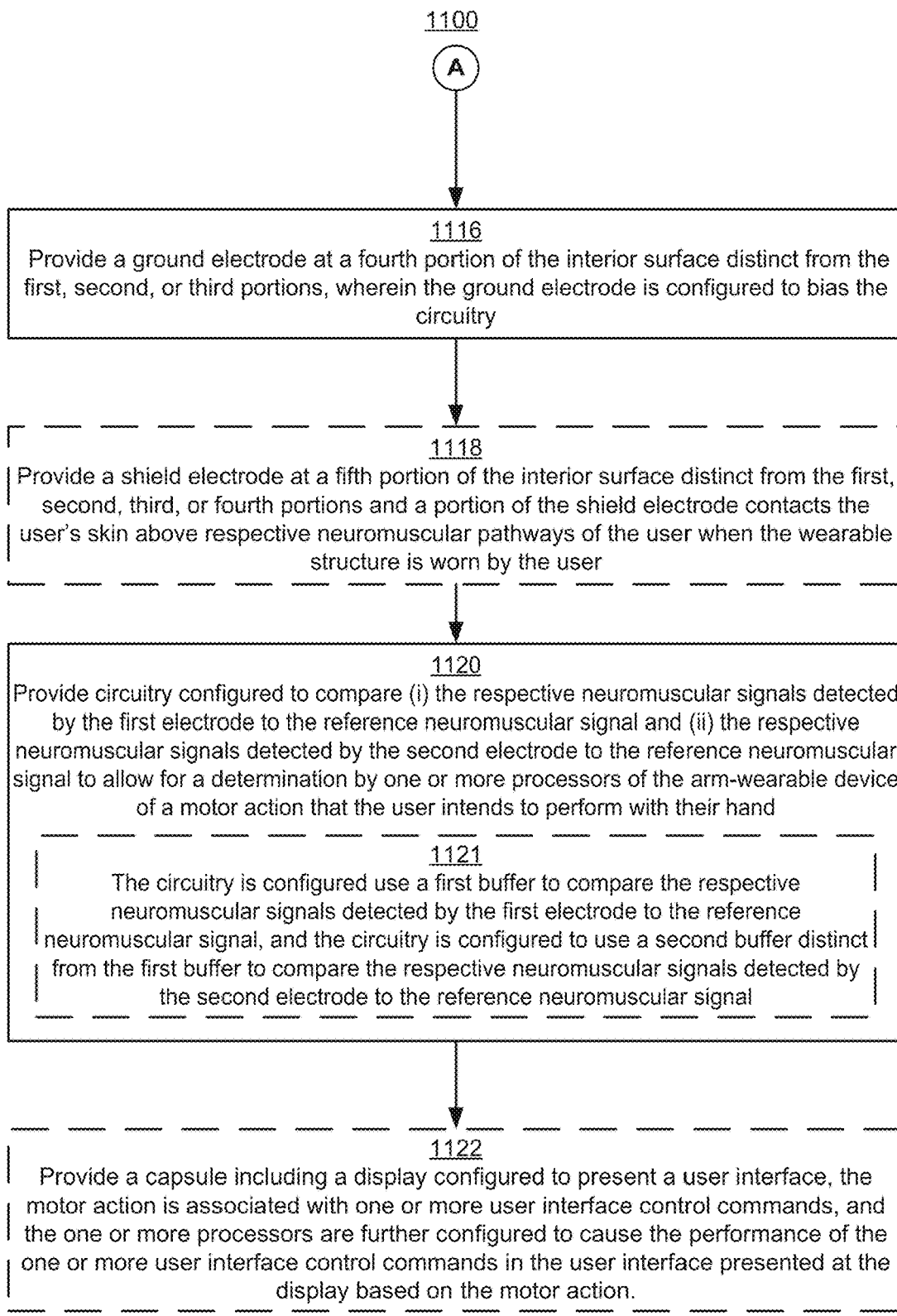

The method 1000 includes comparing (1010), by circuitry (e.g., CPU 1526, MCU 1552, etc.; FIG. 15) of arm-wearable device, (i) the respective neuromuscular signals detected by the first electrode to the reference neuromuscular signal and (ii) the respective neuromuscular signals detected by the second electrode to the reference neuromuscular signal to allow for a determination by one or more processors of the arm-wearable device of a motor action that the user intends to perform with their hand. In some embodiments, the motor action is associated with one or more input commands, and the method 1000 includes providing (1014), by the one or more processors, the one or more input commands associated with the motor action to a computing device to cause the computing device to perform the one or more input commands in an artificial-reality environment. In some embodiments, the motor action is associated with one or more user interface control commands, and the method 1000 includes (1016) causing, by the one or more processors, the performance of the one or more user interface control commands in the user interface presented at a display of a capsule of an arm-wearable device based on the motor action FIGS. 11A and 11B are flow diagrams illustrating a method of manufacturing an arm-wearable device for sensing neuromuscular signals using a shared reference electrode, in accordance with some embodiments. Operations (e.g., steps) of the method 1100 can be performed in a different order. Some operations (e.g., steps) are optional and can be excluded.

The method 1100 includes providing (1102) a wearable structure configured to be worn by a user, the wearable structure having an interior surface and an exterior surface, the interior surface being configured to contact a user's skin when the arm-wearable device is donned by the user. The method also includes providing (1104) a first electrode, a second electrode, and a shared reference electrode. The first electrode is (1106) at a first portion of the interior surface to form, in part, a first channel for detecting neuromuscular signals. The second electrode is (1108) at a second portion, distinct from the first portion, of the interior surface to form, in part, a second channel for detecting neuromuscular signals. The shared reference electrode is (1110) at a third portion, distinct from the first and second portions, of the interior surface for detecting a reference neuromuscular signal that is compared to respective neuromuscular signals detected by the first electrode and the second electrode. In some embodiments, the reference neuromuscular signal is (1112) unbuffered. Alternatively, in some embodiments, the reference neuromuscular signal is (1114) buffered. In some embodiments, each electrode of the first electrode, the second electrode, and the shared reference electrode contacts (1115) the user's skin above respective neuromuscular pathways of the user when the wearable structure is worn by the user. Different block diagrams of the electrode configurations are provided above in reference to FIGS. 1A-4.

The method 1100 includes providing (1116) a ground electrode at a fourth portion of the interior surface distinct from the first, second, or third portions. The ground electrode contacts the user's skin above respective neuromuscular pathways of the user when the wearable structure is worn by the user, and is configured to bias the circuitry.

In some embodiments, the method 1100 includes providing (1118) a shield electrode aligned along a fifth portion of the interior surface distinct from the first, second, third, or fourth portions. A portion of the shield electrode contacts the user's skin above respective neuromuscular pathways of the user when the wearable structure is worn by the user. Examples of the shield electrode and the ground electrode are provided above in reference to FIGS. 2A-4.

The 1100 method includes providing (1120) circuitry configured to compare (i) the respective neuromuscular signals detected by the first electrode to the reference neuromuscular signal and (ii) the respective neuromuscular signals detected by the electrode to the reference neuromuscular signal to allow for a determination by one or more processors of the arm-wearable device of a motor action that the user intends to perform with their hand. In some embodiments, the circuitry is configured to use (1121) a first buffer to compare the respective neuromuscular signals detected by the first electrode to the reference neuromuscular signal, and the circuitry is configured to use a second buffer distinct from the first buffer to compare the respective neuromuscular signals detected by the second electrode to the reference neuromuscular signal. In some embodiments, the first buffer is an instrumentation amplifier or a first differential amplifier and the second buffer is an instrumentation amplifier distinct from the first instrumentation amplifier or a second differential amplifier distinct from the first differential amplifier.

In some embodiments, the method 1100 includes providing (1122) a capsule including a display configured to present a user interface, the motor action is associated with one or more user interface control commands, and the one or more processors are further configured to cause the performance of the one or more user interface control commands in the user interface presented at the display based on the motor action.

Figure 12B:
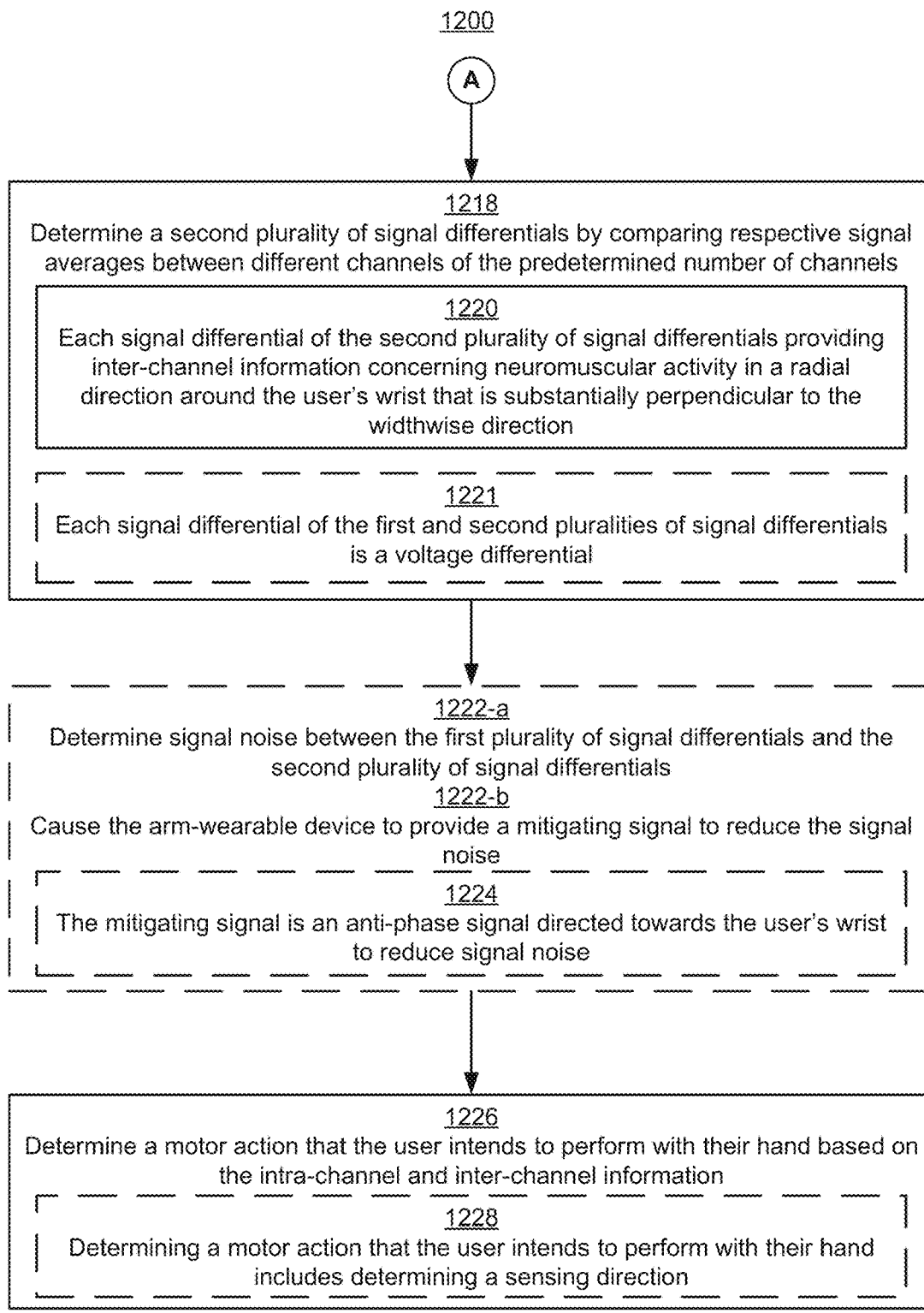

FIGS. 12A and 12B shows a detailed flow diagram of a method 1200 for sensing neuromuscular signals along a radial direction using one or more channels of an arm-wearable device, according to some embodiments. Method 1200 can be performed at any arm-wearable device described above in reference to FIGS. 1A-4 and 6-8B. Operations (e.g., steps) of the method 1200 can be performed by one or more processors (e.g., CPU 1526, MCU 1552, etc.; FIG. 15) of an arm-wearable device. In some embodiments, the arm-wearable device is coupled with one or more sensors (e.g., various sensors shown in FIG. 15, such as a heart rate sensor 1558, EMG sensor 1546, SpO2 sensor 1554, altimeter 1548, thermal sensor or thermal couple, ambient light sensor, ambient noise sensor), a display 1513, a speaker 1574, an image sensor 1570, and a microphone 1572 to perform the one or more operations of FIGS. 12A and 12B. At least some of the operations shown in FIG. 12 correspond to instructions stored in a computer memory or computer-readable storage medium (e.g., storage 1502, ram 1503, and/or memory 1550; FIG. 15). Operations 1202-1228 can also be performed in part using one or more processors and/or using instructions stored in memory or computer-readable medium of an electronic device communicatively coupled to the arm-wearable device (e.g., a smartphone can perform operations 1202-1228 alone or in conjunction with the one or more processors of the arm-wearable device).

The method 1200 includes contacting (1202) a user's skin with the interior surface when the arm-wearable device is donned by the user. The interior surface of the arm-wearable device includes a predetermined number of channels, each channel formed by an electrode at a respective portion of the interior surface. For example, a first channel can be formed by a first electrode 215 when used in conjunction with the shared reference electrode 217 and a second channel can be formed by a second electrode 216 when used in conjunction with the shared reference electrode 217, as discussed above in reference to FIGS. 2A-2D. Each electrode contacts (1204) the user's skin above respective neuromuscular pathways of the user when the wearable structure is worn by the user. In some embodiments, the neuromuscular pathways are (1205)

associated with muscles used for moving each of the user's digits, the user's wrist, and the user's forearm.

The method 1200 includes detecting (1206), via the electrodes forming the predetermined number of channels, neuromuscular signals from the respective neuromuscular pathways of the user. The method 1200 also includes determining (1208) a first plurality of signal differentials between respective neuromuscular signal values sensed by respective electrodes of each respective channel of the predetermined number of channels. Each signal differential of the first plurality of signal differentials provides (1210) intra-channel information concerning neuromuscular activity in a widthwise direction of the interior surface of the wearable structure.

The method 1200 includes determining (1214), for each channel of the predetermined number of channels, a signal average based on the respective neuromuscular signal values sensed by respective electrodes of a respective channel of the predetermined number of channels. In some embodiments, each respective signal average based on respective neuromuscular signal values sensed by respective electrodes of a respective channel of the predetermined number of channels is (1216) an average voltage measured with respect to ground.

The method 1200 includes determining (1218) a second plurality of signal differentials by comparing respective signal averages between different channels of the predetermined number of channels. Each signal differential of the second plurality of signal differentials provides (1220) inter-channel information concerning neuromuscular activity in a radial direction around the user's wrist that is substantially perpendicular to the widthwise direction. In some embodiments, each signal differential of the first and second pluralities of signal differentials is (1221) a voltage differential.

In some embodiments, the method 1200 includes determining (1222-a) signal noise between the first plurality of signal differentials and the second plurality of signal differentials and causing (1222-b) the arm-wearable device to provide a mitigating signal to reduce the signal noise. In some embodiments, the mitigating signal is an anti-phase signal directed (1224) towards the user's wrist to reduce signal noise.

The method 1200 includes determining (1226) a motor action that the user intends to perform with their hand based on the intra-channel and inter-channel information. In some embodiments, determining a motor action that the user intends to perform with their hand includes determining (1228) a sensing direction. Examples of generating the signal differentials is provided above in reference to FIGS. 6-8B.

Figure 13B:
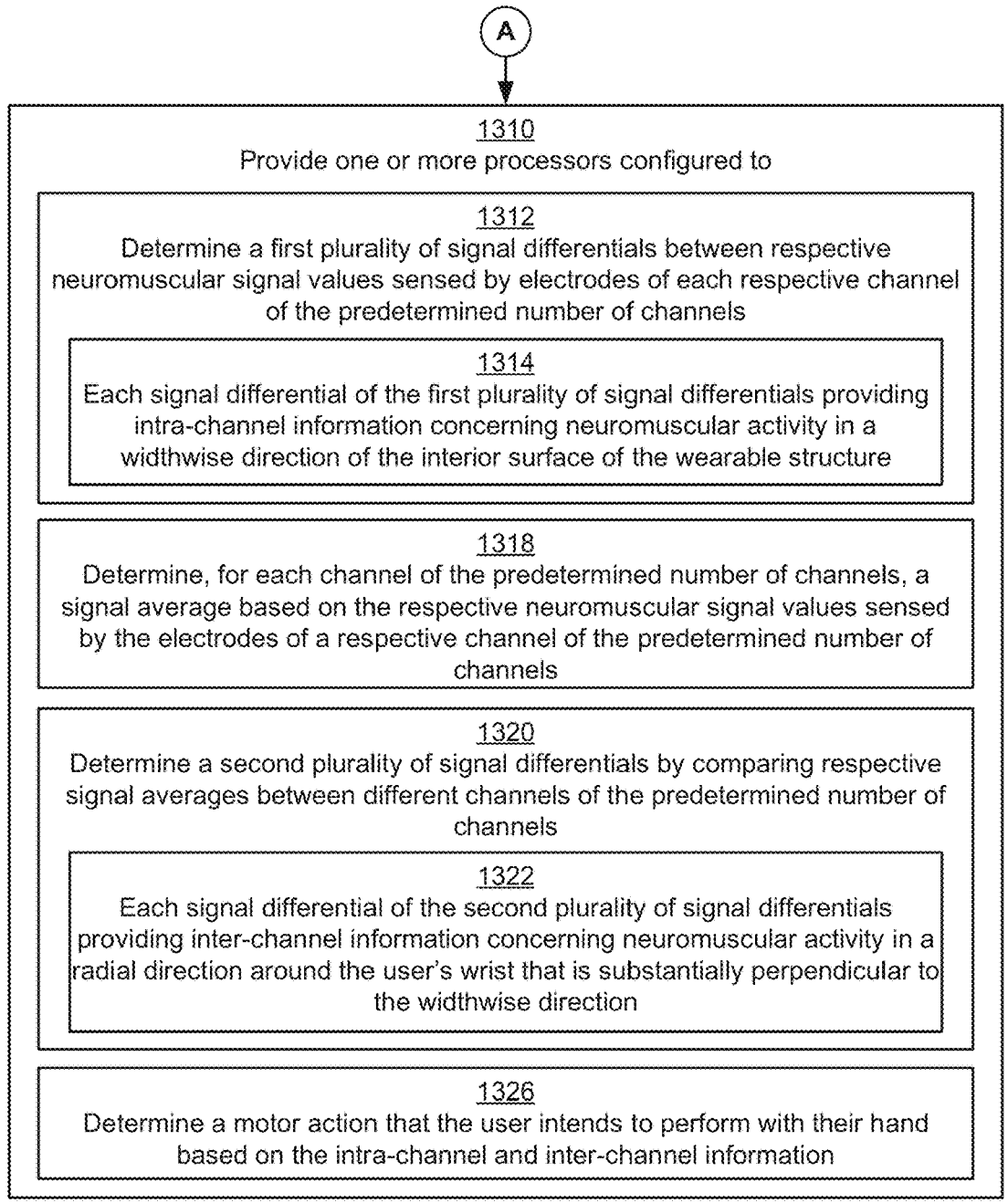

FIGS. 13A and 13B are flow diagrams illustrating a method of manufacturing an arm-wearable device for sensing neuromuscular signals along a radial direction using one or more channels, in accordance with some embodiments. Operations (e.g., steps) of the method 1300 can be performed in a different order. Some operations (e.g., steps) are optional and can be excluded.

The method 1300 includes providing (1302) a wearable structure configured to be worn by a user, the wearable structure having an interior surface and an exterior surface. The interior surface is configured to contact a user's skin when the arm-wearable device is donned by the user. The method 1300 includes providing (1304) a predetermined number of channels, each channel formed by electrodes at a respective portions of the interior surface and configured to detect neuromuscular signals (e.g., a first channel formed by a first electrode 215 and a second channel formed by a second electrode 216, as discussed above in reference to FIGS. 2A-2D). Each electrode contacts (1308) the user's skin above respective neuromuscular pathways of the user when the wearable structure is worn by the user.

The method 1300 includes providing (1310) one or more processors configured to determine (1312) a first plurality of signal differentials between respective neuromuscular signal values sensed by electrodes of each respective channel of the predetermined number of channels. Each signal differential of the first plurality of signal differentials provides (1314) intra-channel information concerning neuromuscular activity in a widthwise direction of the interior surface of the wearable structure. The one or more processors are further configured to determine (1318), for each channel of the predetermined number of channels, a signal average based on the respective neuromuscular signal values sensed by the electrodes of a respective channel of the predetermined number of channels. The one or more processors are also configured to determine (1320) a second plurality of signal differentials by comparing respective signal averages between different channels of the predetermined number of channels. Each signal differential of the second plurality of signal differentials provides (1322) inter-channel information concerning neuromuscular activity in a radial direction around the user's wrist that is substantially perpendicular to the widthwise direction. The one or more processors are configured to determine (1326) a motor action that the user intends to perform with their hand based on the intra-channel and inter-channel information.

Figure 14A:
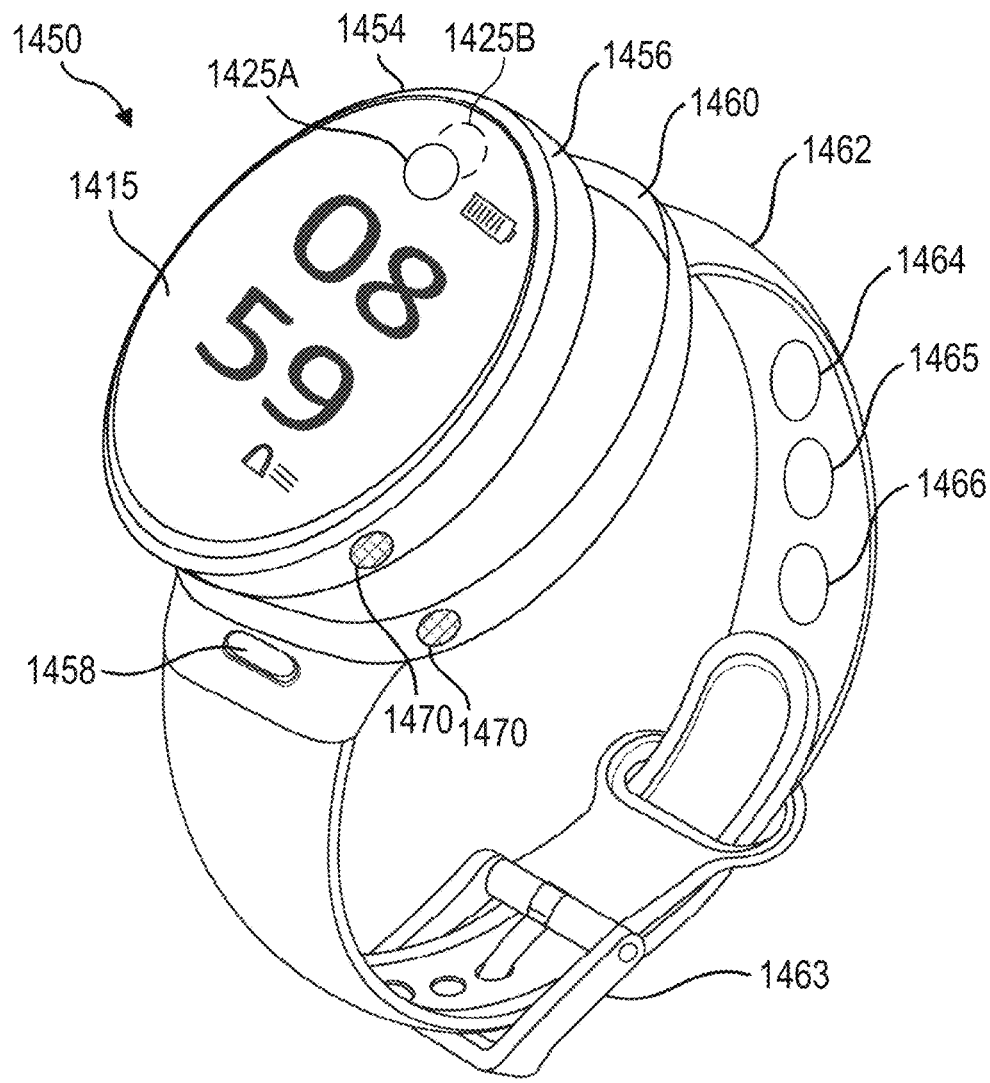
FIGS. 14A and 14B illustrate an example wrist-wearable device, in accordance with some embodiments.
Figure 14B:
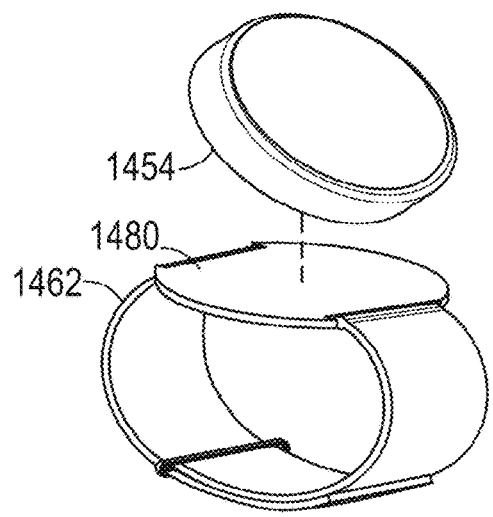
Figure 15:
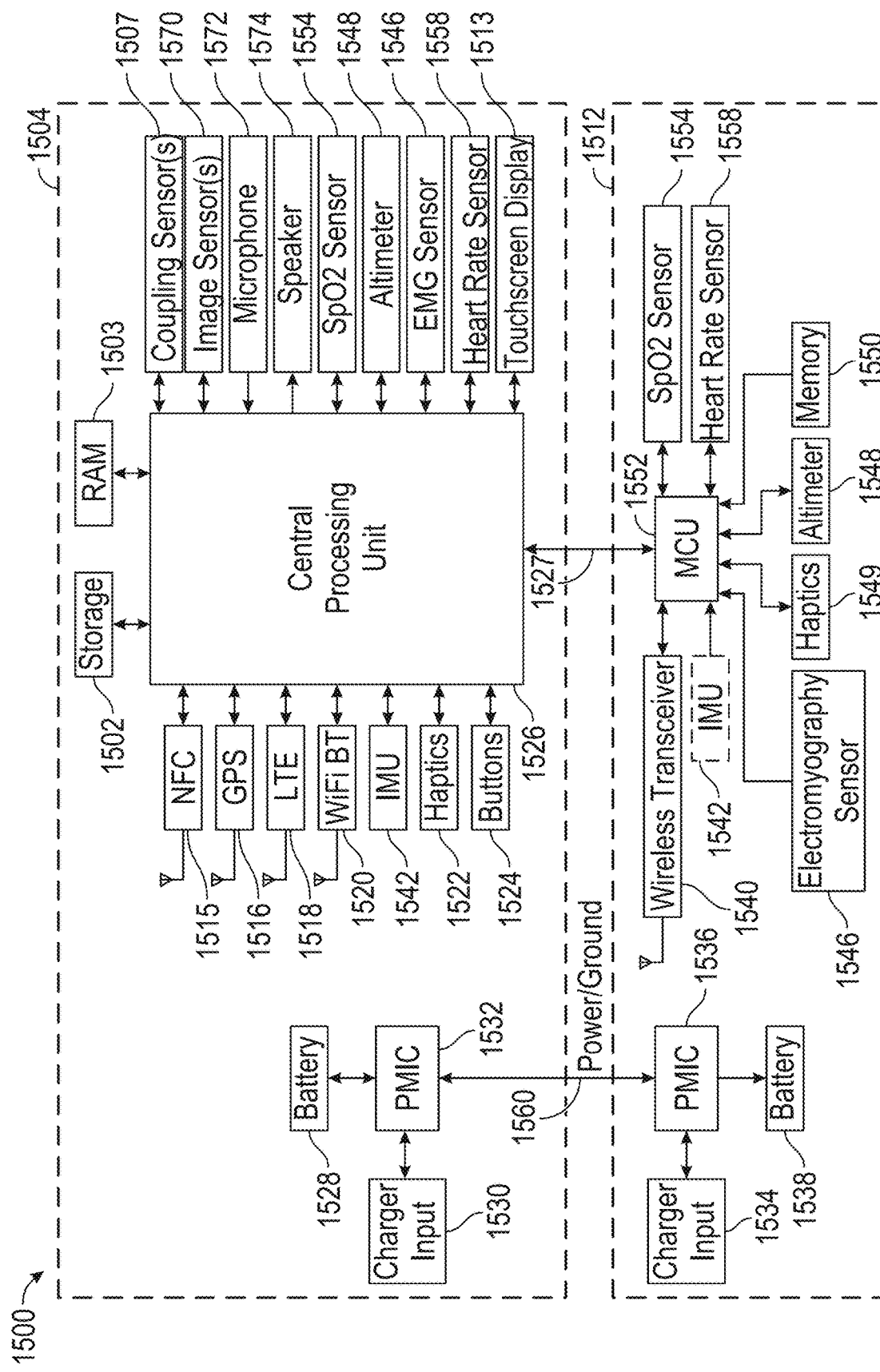
FIG. 15 is a block diagram of a wrist-wearable device system, according to at least one embodiment of the present disclosure.

FIGS. 14A and 14B illustrate an example wrist-wearable device 1450, in accordance with some embodiments. The wrist-wearable device 1450 is any arm-wearable device described above in reference to FIGS. 1A-4, FIGS. 6-8B, or a combination thereof, such that wearable device 110 should be understood to have the features of wearable device 1450 and vice versa. FIG. 14A illustrates a perspective view of the wrist-wearable device 1450 that includes a watch body 1454 decoupled from a watch band 1462. Watch body 1454 and watch band 1462 can have a substantially rectangular or circular shape and can be configured to allow a user to wear the wrist-wearable device 1450 on a body part (e.g., a wrist). The wrist-wearable device 1450 can include a retaining mechanism 1463 (e.g., a buckle, a hook and loop fastener, etc.) for securing watch band 1462 to the user's wrist. The wrist-wearable device 1450 can also include a coupling mechanism 1460 (e.g., a cradle) for detachably coupling capsule or watch body 1454 (via a coupling surface 1456 of the watch body 1454) to watch band 1462.

The wrist-wearable device 1450 can include one or more features and perform various functions associated with the arm-wearable devices described above with reference to FIGS. 1A-9C. As will be described in more detail below with reference to FIG. 15, functions executed by the wrist-wearable device 1450 can include, without limitation, display of visual content to the user (e.g., visual content displayed on display screen 1513), sensing user input (e.g., sensing a touch on button 1458, sensing biometric data on sensor 1464, sensing neuromuscular signals on neuromuscular sensor 1465, etc.), messaging (e.g., text, speech, video, etc.), image capture, wireless communications (e.g., cellular, near field, Wi-Fi, personal area network, etc.), location determination, financial transactions, providing haptic feedback, alarms, notifications, indications, biometric authentication, health monitoring, sleep monitoring, etc. These functions can be executed independently in watch body 1454, independently in watch band 1462, and/or in communication between watch body 1454 and watch band 1462. In some embodiments, functions can be executed on the wrist-wearable device 1450 in conjunction with an artificial-reality environment which includes, but is not limited to, virtual-reality (VR) environments (including non-immersive, semi-immersive, and fully-immersive VR environments), augmented-reality environments (including marker-based augmented-reality environments, markerless augmented-reality environments, location-based augmented-reality environments, and projection-based augmented-reality environments), hybrid reality, and other types of mixed-reality environments. As the skilled artisan will appreciate upon reading the descriptions provided herein, the novel wearable devices described herein can be used with any of these types of artificial-reality environments.

The watch band 1462 can be configured to be worn by a user such that an inner surface of the watch band 1462 is in contact with the user's skin. When worn by a user, sensor 1464 is in contact with the user's skin. The sensor 1464 can be a biosensor that senses a user's heart rate, saturated oxygen level, temperature, sweat level, muscle intentions, or a combination thereof. The watch band 1462 can include multiple sensors 1464 that can be distributed on an inside and/or an outside surface of the watch band 1462. Additionally, or alternatively, the watch body 1454 can include the same or different sensors than the watch band 1462 (or the watch band 1462 can include no sensors at all in some embodiments). For example, multiple sensors can be distributed on an inside and/or an outside surface of watch body 1454. As described below with reference to FIGS. 14, the watch body 1454 can include, without limitation, front-facing image sensor 1425A and/or rear-facing image sensor 1425B, a biometric sensor, an IMU, a heart rate sensor, a saturated oxygen sensor, a neuromuscular sensor(s) (e.g., EMG sensors 1546; FIG. 15), an altimeter sensor, a temperature sensor, a bioimpedance sensor, a pedometer sensor, an optical sensor, a touch sensor, a sweat sensor, etc. The sensor 1464 can also include a sensor that provides data about a user's environment including a user's motion (e.g., an IMU), altitude, location, orientation, gait, or a combination thereof. The sensor 1464 can also include a light sensor (e.g., an infrared light sensor, a visible light sensor) that is configured to track a position and/or motion of watch body 1454 and/or watch band 1462. Watch band 1462 can transmit the data acquired by the sensor 1464 to watch body 1454 using a wired communication method (e.g., a UART, a USB transceiver, etc.) and/or a wireless communication method (e.g., near field communication, Bluetooth™, etc.). Watch band 1462 can be configured to operate (e.g., to collect data using sensor 1464) independent of whether watch body 1454 is coupled to or decoupled from watch band 1462.

The watch band 1462 and/or watch body 1454 can include a haptic device 1466 (e.g., a vibratory haptic actuator) that is configured to provide haptic feedback (e.g., a cutaneous and/or kinesthetic sensation, etc.) to the user's skin. The sensor 1464 and/or haptic device 1466 can be configured to operate in conjunction with multiple applications including, without limitation, health monitoring, social media, game playing, and artificial reality (e.g., the applications associated with artificial reality).

In some examples, the watch band 1462 can include a neuromuscular sensor 1465 (e.g., an electromyography (EMG) sensor, a mechanomyogram (MMG) sensor, a sonomyography (SMG) sensor, etc.). Neuromuscular sensor 1465 can sense a user's intention to perform certain motor actions. The sensed muscle intention can be used to control certain UIs displayed on the display 1415 of the device 1450 and/or can be transmitted to device responsible for rendering an artificial-reality environment (e.g., a head-mounted display) to perform an action in an associated artificial-reality environment, such as to control the motion of a virtual device displayed to the user.

Signals from neuromuscular sensor 1465 can be used to provide a user with an enhanced interaction with a physical object and/or a virtual object in an artificial-reality application generated by an artificial-reality system (e.g., UI objects presented on the display 1415, or another computing device (e.g., a head-mounted display)). Signals from neuromuscular sensor 1465 can be obtained (e.g., sensed and recorded) by one or more neuromuscular sensors 1465 of watch band 1462. Although FIG. 14A shows one neuromuscular sensor 1465, watch band 1462 can include a plurality of neuromuscular sensors 1465 arranged circumferentially on an inside surface of watch band 1462 such that the plurality of neuromuscular sensors 1465 contact the skin of the user. Watch band 1462 can include a plurality of neuromuscular sensors 1465 arranged circumferentially on an inside surface of watch band 1462. Neuromuscular sensor 1465 can sense and record neuromuscular signals from the user as the user performs muscular activations (e.g., movements, gestures, etc.). The muscular activations performed by the user can include static gestures, such as placing the user's hand palm down on a table; dynamic gestures, such as grasping a physical or virtual object; and covert gestures that are imperceptible to another person, such as slightly tensing a joint by co-contracting opposing muscles or using submuscular activations. The muscular activations performed by the user can include symbolic gestures (e.g., gestures mapped to other gestures, interactions, or commands, for example, based on a gesture vocabulary that specifies the mapping of gestures to commands).

In some embodiments, input for performing one or more commands at the wrist-wearable device 1450 are detected based on the neuromuscular signals sensed by the wrist-wearable device 1450. The wrist-wearable device 1450 determines, based on the detected neuromuscular signals a motor action that the user intends to perform or performs with their hand or arm. The motor action can be associated with one or more commands and the one or more processors are further configured to provide the one or more commands associated with the motor action to the wrist-wearable device 1450 to perform the one or more commands. In some embodiments, the motor action is associated with one or more gestures that when detected by the one or more processors are further configured to provide the one or more commands associated with the one or more gestures to the wrist-wearable device 1450 to perform the one or more commands.

Different gestures and motor actions can be determined by the wrist-wearable device 1450. For example, a user can move their wrist, hand, arm, etc. up and down, curl their digits, mimic pressing a digit on the screen, creates a pinch with his hand, etc. When the user performs or intends to perform a motor action or gesture, the wrist-wearable device 1450 detects the neuromuscular signals generated by the user action and determines, using the one or more processors, the motor action or gesture. The wrist-wearable device 1450 then performs an action based on the one or more commands. Alternatively, in some embodiments, the wrist-wearable device 1450 provides one or more commands associated with the motor action or gesture to the computing device (e.g., a computer, a game system, a head-mounted display, a smartphone, etc.) to perform the action. For example, a user can request to use the computing device cellular network to initiate a call, and the wrist-wearable device 1450 can provide a command to the computing device to imitate the call based on the detected motor actions or gestures.

Although the above examples describe gestures such as the movement of digits and pinches, the skilled artisan in this field will appreciate upon reading this disclosure that any number neuromuscular signals can be detected, such as movement of the arm, the elbow, the wrist, individual digits (e.g., the little finger or the thumb), portions of the digits, etc. Further, any number of gestures can be associated with a motor action. For example, instead of a pinch, a confirmation can be a fist, making an open circle with the digits, a double tap, etc.

The wrist-wearable device 1450 can include a coupling mechanism (also referred to as a cradle) for detachably coupling watch body 1454 to watch band 1462. A user can detach watch body 1454 from watch band 1462 in order to reduce the encumbrance of the wrist-wearable device 1450 to the user. The wrist-wearable device 1450 can include a coupling surface 1456 on the watch body 1454 and/or coupling mechanism(s) 1460 (e.g., a cradle, a tracker band, a support base, a clasp). A user can perform any type of motion to couple watch body 1454 to watch band 1462 and to decouple watch body 1454 from watch band 1462. For example, a user can twist, slide, turn, push, pull, or rotate watch body 1454 relative to watch band 1462, or a combination thereof, to attach watch body 1454 to watch band 1462 and to detach watch body 1454 from watch band 1462.

As shown in the example of FIG. 14A, watch band coupling mechanism 1460 can include a type of frame or shell that allows watch body 1454 coupling surface 1456 to be retained within watch band coupling mechanism 1460. Watch body 1454 can be detachably coupled to watch band 1462 through a friction fit, magnetic coupling, a rotation-based connector, a shear-pin coupler, a retention spring, one or more magnets, a clip, a pin shaft, a hook and loop fastener, or a combination thereof. In some examples, watch body 1454 can be decoupled from watch band 1462 by actuation of release mechanism 1470. The release mechanism 1470 can include, without limitation, a button, a knob, a plunger, a handle, a lever, a fastener, a clasp, a dial, a latch, or a combination thereof.

The wrist-wearable device 1450 can include a single release mechanism 1470 or multiple release mechanisms 1470 (e.g., two release mechanisms 1470 positioned on opposing sides of the wrist-wearable device 1450 such as spring-loaded buttons). As shown in FIG. 14A, the release mechanism 1470 can be positioned on watch body 1454 and/or watch band coupling mechanism 1460. Although FIG. 14A shows release mechanism 1470 positioned at a corner of watch body 1454 and at a corner of watch band coupling mechanism 1460, the release mechanism 1470 can be positioned anywhere on watch body 1454 and/or watch band coupling mechanism 1460 that is convenient for a user of wrist-wearable device 1450 to actuate. A user of the wrist-wearable device 1450 can actuate the release mechanism 1470 by pushing, turning, lifting, depressing, shifting, or performing other actions on the release mechanism 1470. Actuation of the release mechanism 1470 can release (e.g., decouple) the watch body 1454 from the watch band coupling mechanism 1460 and the watch band 1462 allowing the user to use the watch body 1454 independently from watch band 1462. For example, decoupling the watch body 1454 from the watch band 1462 can allow the user to capture images using rear-facing image sensor 1425B.

FIG. 14B is a perspective view of another example of the wrist-wearable device 1450. The wrist-wearable devices 1450 of FIG. 14B can include a watch body interface 1480 (another example of a cradle for the capsule portion of the device). The watch body 1454 can be detachably coupled to the watch body interface 1480. Watch body 1454 can be detachably coupled to watch body interface 1480 through a friction fit, magnetic coupling, a rotation-based connector, a shear-pin coupler, a retention spring, one or more magnets, a clip, a pin shaft, a hook and loop fastener, or a combination thereof.

In some examples, watch body 1454 can be decoupled from watch body interface 1480 by actuation of a release mechanism. The release mechanism can include, without limitation, a button, a knob, a plunger, a handle, a lever, a fastener, a clasp, a dial, a latch, or a combination thereof. In some examples, the wristband system functions can be executed independently in watch body 1454, independently in watch body interface 1480, and/or in communication between watch body 1454 and watch body interface 1480. Watch body interface 1480 can be configured to operate independently (e.g., execute functions independently) from watch body 1454. Additionally, or alternatively, watch body 1454 can be configured to operate independently (e.g., execute functions independently) from watch body interface 1480. As will be described in more detail below with reference to the block diagram of FIG. 15, watch body interface 1480 and/or watch body 1454 can each include the independent resources required to independently execute functions. For example, watch body interface 1480 and/or watch body 1454 can each include a power source (e.g., a battery), a memory, data storage, a processor (e.g., a CPU), communications, a light source, and/or input/output devices.

In this example, watch body interface 1480 can include all of the electronic components of watch band 1462. In additional examples, one or more electronic components can be housed in watch body interface 1480 and one or more other electronic components can be housed in portions of watch band 1462 away from watch body interface 1480.

FIG. 15 is a block diagram of a wrist-wearable device system 1500, according to at least one embodiment of the present disclosure. The device 1450 described in detail above is an example wrist-wearable device system 1500, so device 1450 will be understood to include the components shown and described for system 1500 below. The wrist-wearable device system 1500 can have a split architecture (e.g., a split mechanical architecture, a split electrical architecture) between a watch body 1504 (e.g., a capsule) and a watch band 1512 (e.g., a band portion 1462), which was described above in reference to FIGS. 14A and 14B. Each of watch body 1504 and watch band 1512 can have a power source, a processor, a memory, sensors, a charging device, and a communications device that enables each of watch body 1504 and watch band 1512 to execute computing, controlling, communication, and sensing functions independently in watch body 1504, independently in watch band 1512, and/or in communication between watch body 1504 and watch band 1512.

For example, watch body 1504 can include battery 1528, CPU 1526, storage 1502, heart rate sensor 1558, EMG sensor 1546, SpO2 sensor 1554, altimeter 1548, IMU 1542, random access memory 1503, charging input 1530 and communication devices NFC 1515, LTE 1518, and Wi-Fi/Bluetooth™ 1520. Similarly, watch band 1512 can include battery 1538, microcontroller unit 1552, memory 1550, heart rate sensor 1558, EMG sensor 1546, SpO2 sensor 1554, altimeter 1548, IMU 1542, charging input 1534 and wireless transceiver 1540. In some examples, a level of functionality of at least one of watch band 1512 or watch body 1504 can be modified when watch body 1504 is detached from watch band 1512. The level of functionality that can be modified can include the functionality of at least one sensor (e.g., heart rate sensor 1558, EMG sensor 1546, etc.). Each of watch body 1504 and watch band 1512 can execute instructions stored in storage 1502 and memory 1550 respectively that enables at least one sensor (e.g., heart rate sensor 1558, EMG sensor 1546, etc.) in watch band 1512 to acquire data when watch band 1512 is detached from watch body 1504 and when watch band 1512 is attached to watch body 1504.

Watch body 1504 and watch band 1512 can further execute instructions stored in storage 1502 and memory 1550 respectively that enables watch band 1512 to transmit the acquired data to watch body 1504 using wired communications 1527 and/or wireless transceiver 1540. For example, watch body 1504 can display visual content to a user on touchscreen display 1513 (e.g., an instance of display 1415) and play audio content on speaker 1574. Watch body 1504 can receive user inputs such as audio input from microphone 1597 and touch input from buttons 1524. Watch body 1504 can also receive inputs associated with a user's location and/or surroundings. For example, watch body 1504 can receive location information from GPS 1516 and/or altimeter 1548 of watch band 1512.

Watch body 1504 can receive image data from at least one image sensor 1570 (e.g., a camera). Image sensor 147 can include front-facing image sensor 1425A (FIG. 14A) and/or rear-facing image sensor 1425B (FIG. 14B). Front-facing image sensor 1425A and/or rear-facing image sensor 1425B can capture wide-angle images of the area surrounding front-facing image sensor 1425A and/or rear-facing image sensor 1425B such as hemispherical images (e.g., at least hemispherical, substantially spherical, etc.), 180-degree images, 360-degree area images, panoramic images, ultra-wide area images, or a combination thereof. In some examples, front-facing image sensor 1425A and/or rear-facing image sensor 1425B can be configured to capture images having a range between 45 degrees and 360 degrees. Certain input information received by watch body 1504 (e.g., user inputs, etc.) can be communicated to watch band 1512. Similarly, certain input information (e.g., acquired sensor data, neuromuscular sensor data, etc.) received by watch band 1512 can be communicated to watch body 1504.

Watch body 1504 and watch band 1512 can receive a charge using a variety of techniques. In some embodiments, watch body 1504 and watch band 1512 can use a wired charging assembly (e.g., power cords) to receive the charge. Alternatively, or in addition, watch body 1504 and/or watch band 1512 can be configured for wireless charging. For example, a portable charging device can be designed to mate with a portion of watch body 1504 and/or watch band 1512 and wirelessly deliver usable power to a battery of watch body 1504 and/or watch band 1512.

Watch body 1504 and watch band 1512 can have independent power and charging sources to enable each to operate independently. Watch body 1504 and watch band 1512 can also share power (e.g., one can charge the other) via power management IC 1532 in watch body 1504 and power management IC 1536 in watch band 1512. Power management IC 1532 and power management IC 1536 can share power over power and ground conductors and/or over wireless charging antennas.

Wrist-wearable device system 1500 can operate in conjunction with a health monitoring application that acquires biometric and activity information associated with the user. The health monitoring application can be designed to provide information to a user that is related to the user's health. For example, wrist-wearable device system 1500 can monitor a user's physical activity by acquiring data from IMU 1542 while simultaneously monitoring the user's heart rate via heart rate sensor 1558 and saturated blood oxygen levels via SpO2 sensor 1554. CPU 1526 can process the acquired data and display health related information to the user on touchscreen display 1513.

Wrist-wearable device system 1500 can detect when watch body 1504 and watch band 1512 are connected to one another (e.g., mechanically connected and/or electrically or magnetically connected) or detached from one another. For example, pin(s), power/ground connections 1560, wireless transceiver 1540, and/or wired communications 1527, can detect whether watch body 1504 and watch band 1512 are mechanically and/or electrically or magnetically connected to one another (e.g., detecting a disconnect between the one or more electrical contacts of power/ground connections 1560 and/or wired communications 1527). In some examples, when watch body 1504 and watch band 1512 are mechanically and/or electrically disconnected from one another (e.g., watch body 1512 has been detached from watch band 1512 as described with reference to FIGS. 14A and 14B), watch body 1504 and/or watch band 1512 can operate with modified level of functionality (e.g., reduced functionality) as compared to when watch body 1504 and watch band 1512 are mechanically and/or electrically connected to one another. The modified level of functionality (e.g., switching from full functionality to reduced functionality and from reduced functionality to full functionality) can occur automatically (e.g., without user intervention) when wrist-wearable device system 1500 determines that watch body 1504 and watch band 1512 are mechanically and/or electrically disconnected from one another and connected to each other, respectively.

Modifying the level of functionality (e.g., reducing the functionality in watch body 1504 and/or watch band 1512) can reduce power consumption in battery 1528 and/or battery 1538. For example, any of the sensors (e.g., heart rate sensor 1558, EMG sensor 1546, SpO2 sensor 1554, altimeter 1548, etc.), processors (e.g., CPU 1526, microcontroller unit 1552, etc.), communications elements (e.g., NFC 1515, GPS 1516, LTE 1518, Wi-Fi/Bluetooth™ 1520, etc.), or actuators (e.g., haptics 1522, 1549, etc.) can reduce functionality and/or power consumption (e.g., enter a sleep mode) when watch body 1504 and watch band 1512 are mechanically and/or electrically disconnected from one another. Watch body 1504 and watch band 1512 can return to full functionality when watch body 1504 and watch band 1512 are mechanically and/or electrically connected to one another. The level of functionality of each of the sensors, processors, actuators, and memory can be independently controlled.

As described above, wrist-wearable device system 1500 can detect when watch body 1504 and watch band 1512 are coupled to one another (e.g., mechanically connected and/or electrically connected) or decoupled from one another. In some examples, watch body 1504 can modify a level of functionality (e.g., activate and/or deactivate certain functions) based on whether watch body 1504 is coupled to watch band 1512. For example, CPU 1526 can execute instructions that detect when watch body 1504 and watch band 1512 are coupled to one another and activate front-facing image sensor 1425A. CPU 1526 can activate front-facing image sensor 1425A based on receiving user input (e.g., a user touch input from touchscreen display 1513, a user voice command from microphone 1597, a user gesture recognition input from EMG sensor 1546, etc.).

When CPU 1526 detects that watch body 1504 and watch band 1512 are decoupled from one another, CPU 1526 can modify a level of functionality (e.g., activate and/or deactivate additional functions). For example, CPU 1526 can detect when watch body 1504 and watch band 1512 are decoupled from one another and activate rear-facing image sensor 1425B. CPU 1526 can activate rear-facing image sensor 1425B automatically (e.g., without user input) and/or based on receiving user input (e.g., a touch input, a voice input, an intention detection, etc.). Automatically activating rear-facing image sensor 1425B can allow a user to take wide-angle images without having to provide user input to activate rear-facing image sensor 1425B.

In some examples, rear-facing image can be activated based on an image capture criterion (e.g., an image quality, an image resolution, etc.). For example, rear-facing image sensor 1425B can receive an image (e.g., a test image). CPU 1526 and/or rear-facing image sensor 1425B can analyze the received test image data and determine whether the test image data satisfies the image capture criterion (e.g., the image quality exceeds a threshold, the image resolution exceeds a threshold, etc.). Rear-facing image sensor 1425B can be activated when the test image data satisfies the image capture criterion. Additionally, or alternatively, rear-facing image sensor 1425B can be deactivated when the test image data fails to satisfy the image capture criterion.

In some examples, CPU 1526 can detect when watch body 1504 is coupled to watch band 1512 and deactivate rear-facing image sensor 1425B. CPU 1526 can deactivate rear-facing image sensor 1425B automatically (e.g., without user input) and/or based on receiving user input (e.g., a touch input, a voice input, an intention detection, etc.). Deactivating rear-facing image sensor 1425B can automatically (e.g., without user input) reduce the power consumption of watch body 1504 and increase the battery charge time in watch body 1504. In some examples, wrist-wearable device system 1500 can include a coupling sensor 1507 that senses whether watch body 1504 is coupled to or decoupled from watch band 1512. Coupling sensor 1507 can be included in any of watch body 1504, watch band 1512, or watch band coupling mechanism 1460 of FIGS. 14A and 14B. Coupling sensor 1507 (e.g., a proximity sensor) can include, without limitation, an inductive proximity sensor, a limit switch, an optical proximity sensor, a capacitive proximity sensor, a magnetic proximity sensor, an ultrasonic proximity sensor, or a combination thereof. CPU 1526 can detect when watch body 1504 is coupled to watch band 1512 or decoupled from watch band 1512 by reading the status of coupling sensor 1507.

Although the examples provided with reference to FIGS. 1A-15 are discussed in the context of interfaces with EMG sensors, examples may also be implemented in control devices, such as wearable interfaces, used with other types of sensors including, but not limited to, mechanomyography (MMG) sensors, sonomyography (SMG) sensors, and electrical impedance tomography (EIT) sensors. The approaches described herein may also be implemented in wearable interfaces that communicate with computer hosts through wires and cables (e.g., USB cables, optical fiber cables). Further, while the different Further embodiments also include various subsets of the above embodiments including embodiments in FIGS. 1A-15 combined or otherwise re-arranged.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. An arm-wearable device for sensing neuromuscular signals using a shared reference electrode that is shared between two or more electrodes, the arm-wearable device comprising:
    a wearable structure configured to be worn by a user, the wearable structure having an interior surface and an exterior surface, the interior surface being configured to contact a user's skin when the arm-wearable device is donned by the user;
    a first electrode at a first portion of the interior surface for detecting neuromuscular signals;
    a second electrode at a second portion, distinct from the first portion, of the interior surface for detecting neuromuscular signals;
    a shared reference electrode aligned at a third portion, distinct from the first and second portions, of the interior surface for detecting a reference neuromuscular signal that is compared to respective neuromuscular signals detected by the first electrode and the second electrode;
    a ground electrode at a fourth portion of the interior surface distinct from the first, second, and/or third portions, wherein the ground electrode is distinct from the shared reference electrode,
    wherein:
        a portion of each electrode of the first electrode, the second electrode, and the shared reference electrode contacts the user's skin above respective neuromuscular pathways of the user when the wearable structure is worn by the user, and the first electrode and the second electrode each form a respective sensing channel when used in conjunction with the shared reference electrode; and circuitry configured to compare (i) the respective neuromuscular signals detected by the first electrode to the reference neuromuscular signal such that the first electrode and the shared reference electrode are operated as a first sensing channel and (ii) the respective neuromuscular signals detected by the second electrode to the reference neuromuscular signal such that the second electrode and the shared reference electrode are operated as a second sensing channel to allow for a determination by one or more processors of the arm-wearable device of a motor action that the user intends to perform with their hand.

2. The arm-wearable device of claim 1, wherein the shared reference electrode is only one shared reference electrode.

3. The arm-wearable device of claim 1, wherein the shared reference electrode is configured to be positioned above an ulna bone of the user when the arm-wearable device is donned by the user.

4. The arm-wearable device of claim 1, wherein the shared reference electrode is configured to be positioned above a center dorsal side of the user's wrist when the arm-wearable device is donned by the user.

5. The arm-wearable device of claim 1, wherein (i) the respective neuromuscular signals detected by the first electrode and the second electrode and (ii) the reference neuromuscular signal are detected along a same axis of the user's wrist.

6. The arm-wearable device of claim 1, wherein the reference neuromuscular signal is configured to be buffered before it is compared to the respective neuromuscular signals detected by the first electrode and the second electrode, wherein the buffering of the reference neuromuscular signal is configured to reduce effects of noise and interference coupling in signals detected via the shared reference electrode.

7. The arm-wearable device of claim 1, wherein the circuitry is configured use a first buffer to compare the respective neuromuscular signals detected by the first electrode to the reference neuromuscular signal, and the circuitry is configured to use a second buffer distinct from the first buffer to compare the respective neuromuscular signals detected by the second electrode to the reference neuromuscular signal.

8. The arm-wearable device of claim 7, wherein the first buffer is an instrumentation amplifier or a differential amplifier, and the second buffer is an instrumentation amplifier or a differential amplifier.

9. The arm-wearable device of claim 1, wherein:

the first and second electrodes for detecting neuromuscular signals are part of no more than fifteen electrodes for sensing neuromuscular signals, each of the no more than fifteen electrodes including respective electrodes at a distinct portion of the wearable structure, and the circuitry is configured to compare respective neuromuscular signals detected by the respective electrodes of each of the no more than fifteen electrodes to the reference neuromuscular signal to allow for the determination by one or more processors of the arm-wearable device of the motor action that the user intends to perform with their hand.

10. The arm-wearable device of claim 9, wherein the no more than fifteen electrodes comprise six electrodes.

11. The arm-wearable device of claim 1, wherein the ground electrode is configured for common mode rejection.

12. The arm-wearable device of claim 11, further comprising:

a shield electrode at a fifth portion of the interior surface distinct from the first, second, third, or fourth portions, wherein a portion of the shield electrode contacts the user's skin above respective neuromuscular pathways of the user when the wearable structure is worn by the user.

13. The arm-wearable device of claim 1, wherein the motor action is associated with one or more input commands, and the one or more processors are further configured to:

provide the one or more input commands associated with the motor action to a computing device to cause the computing device to perform the one or more input commands in an artificial-reality environment.

14. The arm-wearable device of claim 1, wherein the motor action is associated with one or more user interface control commands, and the arm-wearable device further comprises:

a capsule including a display configured to present a user interface; and wherein the one or more processors are further configured to cause the performance of the one or more user interface control commands in the user interface presented at the display based on the motor action.

15. A non-transitory, computer-readable storage medium including instructions that, when executed by an arm-wearable device including (i) a wearable structure configured to be worn by a user, the wearable structure having an interior surface and an exterior surface, (ii) a first electrode at a first portion of the interior surface, (iii) a second electrode at a second portion, distinct from the first portion, of the interior surface, (iv) a shared reference electrode at a third portion, distinct from the first and second portions, of the interior surface, (v) a ground electrode, distinct from the shared reference electrode, at a fourth portion of the interior surface distinct from the first, second, and/or third portions, cause the arm-wearable device to perform or cause performance of:

comparing respective neuromuscular signals detected by the first electrode to a reference neuromuscular signal, wherein:

the first electrode is configured to contact a user's skin when the arm-wearable device is donned by the user for detecting neuromuscular signals, and the shared reference electrode is configured to contact the user's skin when the arm-wearable device is donned by the user for detecting the reference neuromuscular signal, wherein the shared reference electrode when used in conjunction with the first electrode forms a first sensing channel;

comparing respective neuromuscular signals detected by the second electrode to the reference neuromuscular signal, wherein:

the second electrode is configured to contact the user's skin when the arm-wearable device is donned by the user for detecting neuromuscular signals, wherein the shared reference electrode when used in conjunction with the second electrode forms a second sensing channel distinct from the first sensing channel; and determining a motor action that the user intends to perform with their hand based, in part, on (i) the comparison of the respective neuromuscular signals detected by the first electrode to the reference neuromuscular signal such that the first electrode and the shared reference electrode are operated as the first sensing channel, and (ii) the comparison of the respective neuromuscular signals detected by the second electrode to the reference neuromuscular signal such that the second electrode and the shared reference electrode are operated as the second sensing channel.

16. The non-transitory, computer-readable storage medium of claim 15, wherein the shared reference electrode is configured to be positioned above an ulna bone of the user when the arm-wearable device is donned by the user.

17. The non-transitory, computer-readable storage medium of claim 15, wherein the shared reference electrode is configured to be positioned above a center dorsal side of the user's wrist when the arm-wearable device is donned by the user.

18. A method for sensing neuromuscular signals using a shared reference electrode that is shared between two or more electrodes, the method comprising:

at an arm-wearable device comprising (i) a wearable structure configured to be worn by a user, the wearable structure having an interior surface and an exterior surface, (ii) a first electrode at a first portion of the interior surface, (iii) a second electrode at a second portion, distinct from the first portion, of the interior surface, (iv) a shared reference electrode at a third portion, distinct from the first and second portions, of the interior surface, (v) a ground electrode, distinct from the shared reference electrode, at a fourth portion of the interior surface distinct from the first, second, and/or third portions, and (vi) circuitry:

contacting a user's skin with the interior surface when the arm-wearable device is donned by the user, wherein:

each electrode of the first electrode, the second electrode, and the shared reference electrode contacts the user's skin above respective neuromuscular pathways of the user when the wearable structure is worn by the user, and the first electrode and the second electrode each form a respective sensing channel when used in conjunction with the shared reference electrode;

detecting, via the first and second electrodes, neuromuscular signals from the respective neuromuscular pathways of the user;

detecting, via the shared reference electrode, a reference neuromuscular signal that is compared to respective neuromuscular signals detected by the first electrode and the second electrode;

comparing, by the circuitry, (i) the respective neuromuscular signals detected by the first electrode to the reference neuromuscular signal such that the first electrode and the shared reference electrode are operated as a first sensing channel and (ii) the respective neuromuscular signals detected by the second electrode to the reference neuromuscular signal such that the second electrode and the shared reference electrode are operated as a second sensing channel to allow for a determination by one or more processors of the arm-wearable device of a motor action that the user intends to perform with their hand.

19. The arm-wearable device of claim 1, wherein the circuitry is further configured to:

dynamically form a sensing channel using the shared reference electrode and at least one other electrode.

20. The arm-wearable device of claim 19, wherein the arm-wearable device further comprises a third electrode at a sixth portion of the interior surface distinct from the first, second, third, and/or fourth portions and dynamically forming a sensing channel using the shared reference electrode and the at least one other electrode includes:

supplementing the first sensing channel or the second sensing channel with the third electrode.

* * * * *